US008361802B2

(12) United States Patent
Koide et al.

(10) Patent No.: US 8,361,802 B2
(45) Date of Patent: Jan. 29, 2013

(54) FLUORESCENT OZONE SENSOR

(75) Inventors: Kazunori Koide, Pittsburgh, PA (US); Amanda L. Garner, San Diego, CA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 324 days.

(21) Appl. No.: 12/660,997

(22) Filed: Mar. 9, 2010

(65) Prior Publication Data
US 2010/0255525 A1 Oct. 7, 2010

Related U.S. Application Data

(60) Provisional application No. 61/158,489, filed on Mar. 9, 2009.

(51) Int. Cl.
*G01N 33/00* (2006.01)
(52) U.S. Cl. .................................. 436/135; 436/172
(58) Field of Classification Search ................ 436/135, 436/172
See application file for complete search history.

(56) References Cited

U.S. PATENT DOCUMENTS

| 3,397,966 | A | * | 8/1968 | Plantz ............................ 436/135 |
| 3,975,159 | A | * | 8/1976 | van Heusden ................. 436/135 |
| 4,788,282 | A |   | 11/1988 | Deziel |
| 4,845,030 | A | * | 7/1989 | Batz et al. ....................... 435/28 |
| 4,859,607 | A | * | 8/1989 | Lambert et al. ............... 436/135 |
| 5,116,759 | A |   | 5/1992 | Klainer et al. |
| 5,434,272 | A | * | 7/1995 | Corrie et al. ................... 548/525 |
| 5,529,660 | A |   | 6/1996 | Kogan et al. |
| 6,117,685 | A | * | 9/2000 | Omatsu et al. ................ 436/135 |
| 6,455,320 | B1 |  | 9/2002 | Danz et al. |
| 6,800,765 | B2 |  | 10/2004 | Diwu et al. |
| 7,087,766 | B2 |  | 8/2006 | Nagano et al. |
| 7,160,732 | B2 |  | 1/2007 | Lippard et al. |
| 2003/0153027 | A1 | * | 8/2003 | Nagano et al. .................. 435/25 |
| 2008/0014602 | A1 | * | 1/2008 | Nagano et al. .................. 435/18 |
| 2008/0274492 | A1 | * | 11/2008 | Koide et al. ..................... 435/29 |

OTHER PUBLICATIONS

Hurd, C. D. et al, Journal of the American Chemical Society 1937, 59, 112-117.*
Raulins, N. R. et al, Journal of Organic Chemistry 1961, 1382-1386.*
Schelhaas, M. et al, Angewandte Chemie International Edition in English 1996, 35, 2056-2083.*
Setsukinai, K. et al, Journal of the Chemical Society Perkin Transactions 2 2000, 2453-2457.*
Setsukinai, K. et al, Journal of Biological Chemistry 2003, 278, 3170-3175.*
Gao, W. et al, Journal of the American Chemical Society 2003, 125, 11146-11147.*
Babior, B.M., et al., Investigating antibody-catalyzed ozone generation by human neutrophils. Proc. Natl. Acad. Sci. USA, vol. 100 (6), pp. 3031-3034 (2003).
Bailey, P.S., Ozonation in organic chemistry. vol. I, Ch. VII, Olefinic Compounds. Academic Press, New York, 1978, pp. 83-130.
Chang, M.C.Y., et al., A selective, cell-permeable optical probe for hydrogen peroxide in living cells. J. Am. Chem. Soc. 126, pp. 15392-15393 (2004).
Clennan, E.L., et al., Advances in singlet oxygen chemistry. Tetrahedron 61, Rpt. 723, pp. 6665-6691 (2005).

(Continued)

*Primary Examiner* — Arlen Soderquist
(74) *Attorney, Agent, or Firm* — David G. Oberdick; Peter J. Borghetti

(57) ABSTRACT

A selective, fluorescent "turn-on" probe and method for the detection of ozone in biological and atmospheric samples, wherein the method of detecting ozone in a sample comprises the steps of (1) contacting the sample with a fluorophore capable of undergoing allylic ether or allylic ester cleavage and (2) detecting fluorescence in the sample.

39 Claims, 18 Drawing Sheets

OTHER PUBLICATIONS

Deisseroth, A., et al., Catalase: physical and chemical properties, mechanism of catalysis, and physiologicla role. Physiol. Rev, vol. 50 (3), pp. 319-375 (1970).

Ely, J.C., et al., Implications of platinum-group element accumulation along U. S. roads from catalytic-converter attrition. Environ. Sci. Technol. vol. 35, pp. 3816-3822 (2001).

Garner, A.L., et al., Enhancement of a catalysis-based fluorometric detection method for palladium through rational fine-tuning . . . , J. Am. Chem. Soc., pp. 5163-5171 (2009).

Garner, A.L., et al., Fluorescent method for platinum detection in buffers and serums for cancer medicine and occupational hazards, Chem. Commun, pp. 83-85 (2009).

Garner, A.L. et al., Studies of fluorogenic probe for palladium and platinum leading to a palladium-specific detection method, Chem. Commun, pp. 86-88 (2009).

Garner, A.L., et al., Oxidation state-specific fluorescent method for palladium(II) and platinum(IV) based on the catalyzed aromatic . . . , J. Am. Chem. Soc., 130, 16472-73, 2008.

Horvath, M., et al., Ozone. Elsevier, NY, pp. 108-110, (1985).

Imlay, J.A., Cellular defenses against superoxide and hydrogen peroxide, Annu. REv. Biochem, vol. 77, pp. 755-776 (2008).

Jiménez, A.M., et al., Air analysis: determination of ozone by chemiluminescence. Appl. Spectros. Rev. vol. 32 (1&2), pp. 141-149 (1997).

Kettle, A.J., et al., Do neutrophils produce ozone? An appraisal of current evidence. BioFactors, vol. 24, pp. 41-45 (2005).

Kettle, A.J., et al., Superoxide converts indigo carmine to isatin sulfonic acid. J. Biol. Chem. vol. 279(18), pp. 118521-118525 (2004).

Koide, K., et al., Scalable and concise synthesis of dichlorofluorescein derivatives displaying tissue permeation in live zebrafish embryos, ChemBioChem, vol. 9, 214-18 (2008).

Kuczkowski, R.L., 1,3-Dipolar cycloaddition chemistry, vol. 2 (ed. Padwa, A.) pp. 197-271, John Wiley & Sons, NY (1984).

Li, J. et al., Atmospheric ozone measurement with an inexpensive and fully automated porous tube collector-colorimeter, Talanta, vol. 74, pp. 958-964 (2008).

Maruo, Y.Y., Measurement of ambient ozone using newly developed porous glass sensor, Sens. Actuat, B. 126, pp. 485-491 (2007).

Miller, E.W., et al., Molecular imaging of hydrogen peroxide produced for cell signaling, Nature Chem. Biol., vol. 3, pp. 263-267 (2007).

Mudway, I.S., et al., Ozone and the lung: a sensitive issue. Mol. Aspects Med., vol. 21, pp. 1-48 (2000).

Mueller, S., et al., Determination of catalase activity at physiological hydrogen peroxide concentrations, Anal. Biochem., vol. 245, pp. 55-60 (1997).

Nemec, A.A., et al., Nickel mobilizes intracellular zinc to induce metallothionein in human airway epithelial cells, Am. J. Respir. Cell Mol Biol., vol. 41, pp. 69-75 (2009).

Parrish, D.D., et al., Methods for gas-phase measurements of ozone, ozone precursors and aerosol precursors. Atmos. Environ., vol. 34, pp. 1921-1957 (2000).

Pryor, W.A., How far does ozone penetrate into the pulmonary air/tissue boundary before it reacts? Free Radical Biol. Med., vol. 12, pp. 83-88 (1992).

Pryor, W.A., Mechanisms of radical formation from reactions of ozone with target molecules in the lung. Free Radical Biol. Med., vol. 17, pp. 461-465 (1994).

Pryor, W.A., Free radical biology and medicine: it's a gas, man! Am. J. Physiol Regul Integr Comp Physiol, vol. 291, pp. R491-R511 (2006).

Sawyer, D.T., et al., How super is superoxide? Acc. Chem. Res., vol. 14, pp. 393-400 (1981).

Sies, H., Ozone in arteriosclerotic plaques: searching for the "smoking gun". Angew. Chem. Int. Ed., vol. 43, pp. 3514-3515 (2004).

Smith, L.L., Oxygen, oxysterols, ouabain, and ozone: a cautionary tale. Free Radical Biol. Med., vol. 37(3), pp. 318-324 (2004).

Soh, N., Recent advances in fluorescent probes for the detection of reactive oxygen species. Anal. Bioanal. Chem., vol. 386, pp. 532-543 (2006).

Soini, E., et al., Fluoroimmunoassay: present status and key problems. Clin. Chem. vol. 25(3), pp. 353-361 (1979).

Song, F., et al., A highly sensitive fluorescent sensor for palladium based on the allylic oxidative insertion mechanism. J. Am. Chem. Soc., vol. 129, pp. 12354-12355 (2007).

Song, F., et al., Oxidation-resistant fluorogenic probe for mercury based on alkyne oxymercuration. J. Am. Chem. Soc., vol. 130, pp. 16460-16461 (2008).

Takeuchi, K., et al., Quantitative determination of aqueous-phase ozone by chemiluminescence using indigo-5,5'-disulfonate. Anal. Chem. vol. 61, pp. 619-623 (1989).

Uchiyama, S, et al., Simultaneous determination of ozone and carbonyls using trans-1,2-bis (4-pyridyl)ethylene as an ozone scrubber . . . Anal. Chem., vol. 80, pp. 3285-3290 (2008.

Wentworth, Jr., P., et al., Evidence for antibody-catalyzed ozone formation in bacterial killing and inflammation. Science, vol. 298, pp. 2195-2199 (2002).

Wentworth, Jr., P., et al., Evidence for ozone formation in human atherosclerotic arteries. Science, vol. 302, pp. 1053-1056 (2003).

Weschler, C.J., Ozone's impact on public health: contributions from indoor exposures to ozone and products of ozone-initialed chemistry. Environ. Health Perspect. 114, 1489-96, 2006.

Weschler, C.J., Ozone in indoor environments: concentration and chemistry, Indoor Air, vol. 10, pp. 269-288 (2000).

Williams, EJ., et al., Comparison of ultraviolet absorbance, chemiluminescence, and DOAS instruments for Ambient Ozone . . . Environ. Sci. Technol. vol. 40, pp. 5755-5762 (2006).

Yamashita, K., et al., Ozone production by amino acids contributes to killing of bacteria, Proc. Natl Acad. Sci. USA, vol. 105(44), pp. 16912-16917 (2008).

Garner, A.L., et al., Specific fluorogenic probes for ozone in biological and atmospheric samples, Nature Chem., vol. 1, pp. 316-321 (2009).

Aubry, J.M., et al., Chemical sources of singlet oxygen. Peroxidation of water-soluble singlet oxygen carriers with the hydrogen . . . , J. Org. Chem. vol. 54, pp. 726-728 (1989).

Domaille, D.W., et al., Synthetic fluorescent sensors for studying the cell biology of metals. Nat. Chem. Biol., vol. 4(3), pp. 168-175 (2008).

Mudway, I.S., et al. Antioxidant consumption and repletion kinetics in nasal lavage fluid following exposure of healthy human . . . , Eur. Respir. J. vol. 13, pp. 1429-1438 (1999).

Rotman, B., Measurement of activity of single molecules of b-D-galactosidase, Proc. Natl. Acad. Sci. U.S.A. vol. 47, pp. 1981-1991 (1961).

* cited by examiner

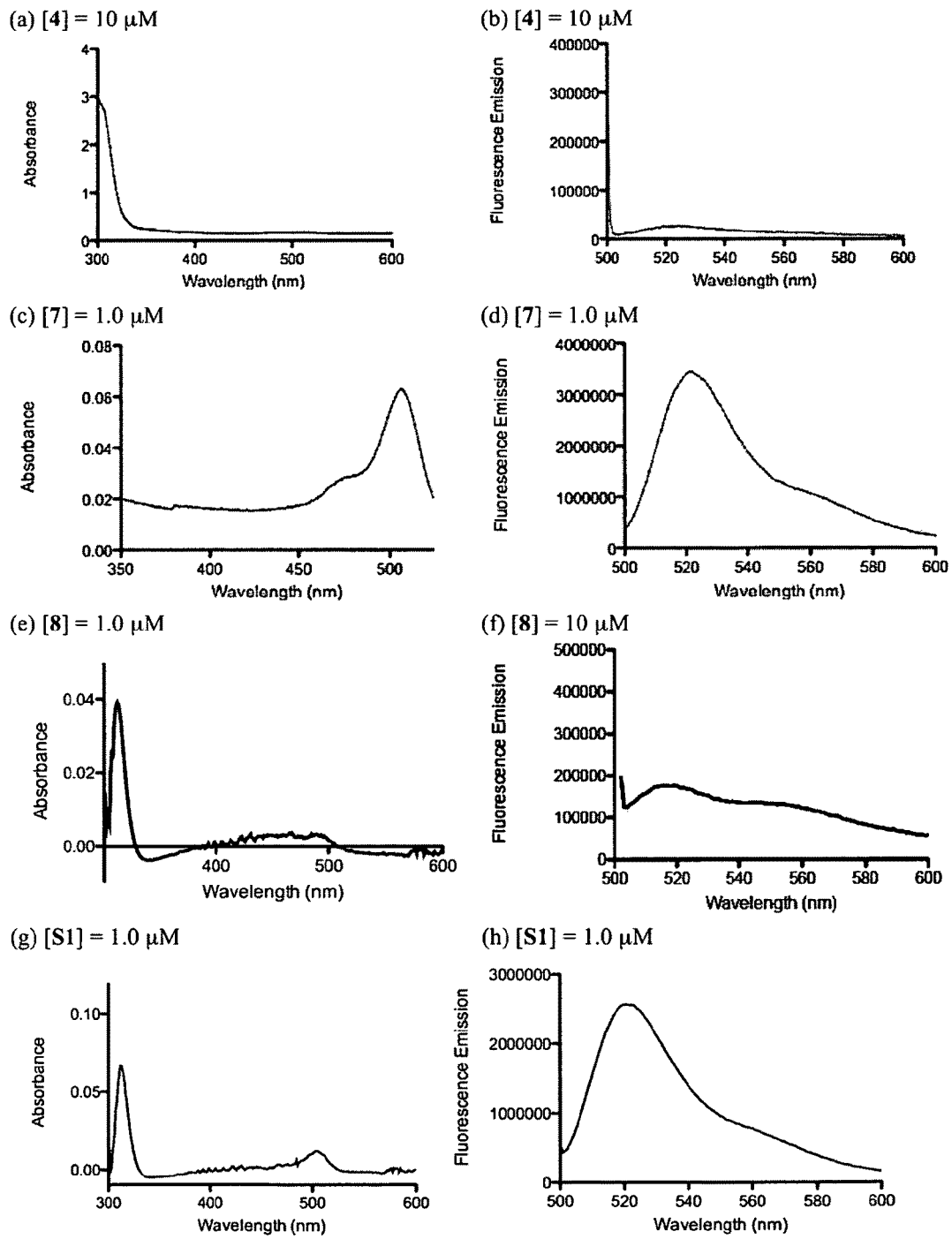
Figures 4A-H

¹H NMR spectrum of compound 3: CDCl₃, 293K, 300 MHz

¹³C NMR spectrum of compound 3: CDCl₃, 293K, 75 MHz

¹H NMR spectrum of compound 4: CDCl₃, 293K, 300 MHz

¹³C NMR spectrum of compound 4: CDCl₃, 293K, 75 MHz

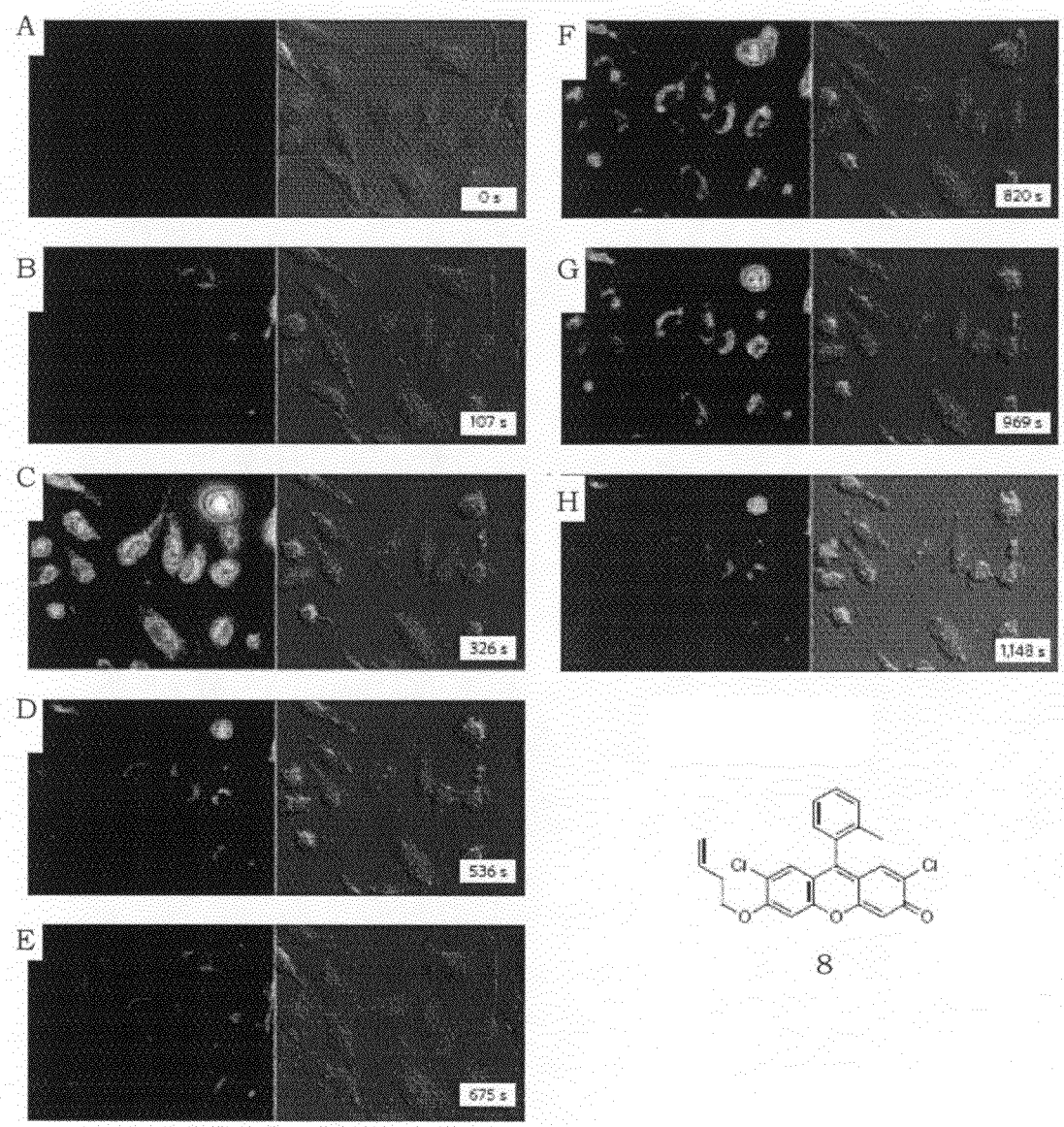
Figs. 16A-H

FLUORESCENT OZONE SENSOR

CROSS REFERENCE TO RELATED APPLICATIONS

The present invention claims benefit of U.S. Provisional Application Ser. No. 61/158,489, entitled "DETECTION OF OZONE WITH FLUORPHORES VIA ALLYLIC OXIDATIVE INSERTION" filed on Mar. 9, 2009, which is incorporated herein by reference.

STATEMENT REGARDING FEDERALLY SPONSORED RESEARCH OR DEVELOPMENT

The invention was made with government support under Federal Grants Number CHE-0616577 awarded by the National Science Foundation. The United States Government has certain rights to the invention.

FIELD OF THE INVENTION

The present invention relates to fluorogenic compounds that can be used as sensors for detection of ozone via an allylic oxidative insertion reaction.

BACKGROUND OF THE INVENTION

Ozone exposure is a growing global health problem, especially in urban areas. While ozone in the stratosphere protects the earth from damaging ultraviolet light, tropospheric or ground level ozone is toxic resulting in damage to the respiratory tract and the exact mechanism by which ozone damages the respiratory system is poorly understood. It has been shown that ozone may be produced endogenously in inflammation and antibacterial responses of the immune system; however, these results have sparked controversy due to the use of a non-specific colorimetric probe.

Reactive oxygen species (ROS) have had a rather controversial history. The existence of singlet oxygen and superoxide was first proposed in the late 1960s; however, due to the lack of sensitive and specific probes these results were met with skepticism, and these observations were only confirmed in the late 1980s. Research indicates that ozone is produced endogenously from singlet oxygen in both neutrophils and atherosclerotic plaque implicating ozone in inflammatory responses. This conclusion was drawn from the premise that the colorimetric dye, indigo carmine 1 (See FIG. 1), differentially reacted with ozone as opposed to other ROS. However, similar to the singlet oxygen/superoxide story, the colorimetric dye, indigo carmine 1 has since been proven to not only react with ozone but also with superoxide in a similar manner, thus, calling into questions these findings of endogenous ozone.

Chemiluminescent methods, including the use of the colorimetric dye, indigo carmine 1, have also been used to measure ozone in ambient air; however, other atmospheric compounds are known to also absorb in this region of the electromagnetic spectrum and false-positive ozone readings are often reported. In addition, many of these methods are sensitive to humidity.

There are several problems associated with the use of the colorimetric dye, indigo carmine 1 as a specific sensor for ozone. First, the dye readily undergoes oxidative cleavage, which is most likely responsible for the lack of specificity. Additionally, the reaction of blue with ROS yields compound 2 (See FIG. 1), which is colorless and cannot be directly visualized without the use of a spectrometer. In biological samples, high-performance liquid chromatography (HPLC) or mass spectrometry are often required in combination with such spectroscopic techniques because the signal for compound 2 (UV: $\lambda_{max}$=245 and 298 nm) overlaps with many other bioorganic compounds.

Useful sensors generate virtually no signal in the absence of an analyte, while producing a strong signal in its presence. Small molecule-based fluorescent sensors are particularly useful because they possess spectral properties that are easily discernable and are often soluble in aqueous media. Also, fluorescent samples can be visualized easily with the aid of a hand-held fluorescent spectrometer, fluorescent microscope or even a simple hand-held laser pen.

SUMMARY OF THE INVENTION

The present invention is a selective, fluorescent "turn-on" probe for the detection of ozone in biological and atmospheric samples.

In some aspects, the present invention provides a method of detecting ozone in a sample comprising the steps of 1) contacting the sample with a fluorophore capable of undergoing allylic ether or allylic ester cleavage; and 2) detecting fluorescence in the sample.

In some aspects the present invention provides methods of detecting ozone in a sample comprising contacting a sample with a compound having the formula

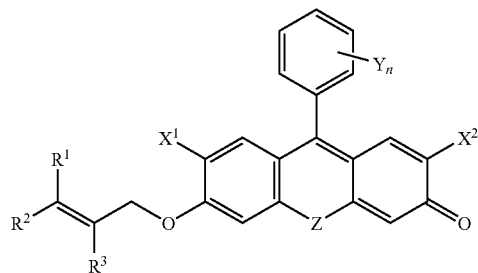

(I)

where $X^1$ and $X^2$ are each independently hydrogen, an homoallyl group, or halogen;
Z is O, S, Se, or NR', wherein R' is hydrogen or an homoallyl group;
n is an integer from 1 to 5;
each Y is independently hydrogen, or a functional group as that term is understood in the art; and
$R^1$, $R^2$, and $R^3$ are independently either hydrogen or homoallyl or aryl groups that may contain one or more further substitutions; and
detecting fluorescence in the sample.

In another aspect, the present invention provides methods of detecting ozone in a sample comprising contacting the sample with a compound of formula (II):

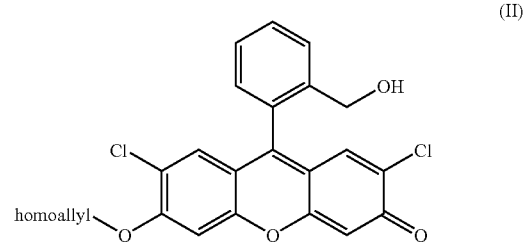

(II)

detecting fluorescence in the sample.

In another aspect, the present invention provides methods of detecting ozone in a sample comprising contacting the sample with a compound of formula (III):

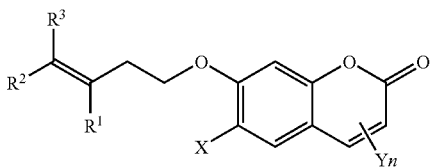

where n=1 or 2 and $R^1$, $R^2$, $R^3$, X (as $X^1$ or $X^2$) and Y are as defined above; and detecting fluorescence in the sample.

In yet another aspect, the present invention provides methods of detecting ozone in a sample comprising contacting a sample with a compound of formula (IV):

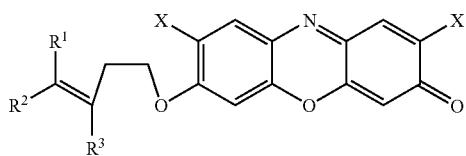

where n=1 or 2 and $R^1$, $R^2$, $R^3$, X and Y are as defined above; and detecting fluorescence in the sample.

BRIEF DESCRIPTION OF THE DRAWINGS

FIGS. 4A-H illustrate absorbance and fluorescence emission of compounds 4, 7, 8, and S1;

FIGS. 16A-H are photographs of live-cell imaging of human bronchial epithelial cells in the presence of ozone using compound 8.

DETAILED DESCRIPTION OF THE INVENTION

Figure 1:
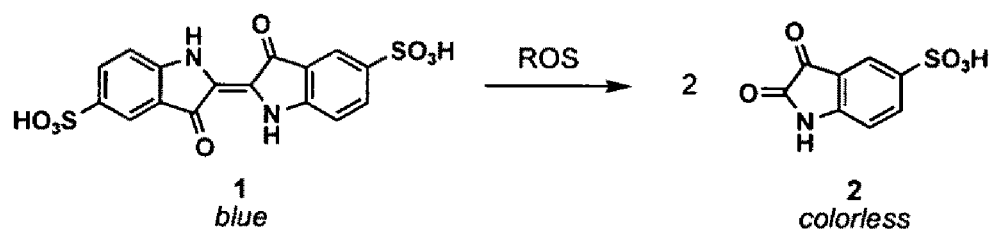
FIG. 1 illustrates nonselective indigo carmine sensor for Reactive Oxygen Species (ROS)

As used herein in the specification and claims, including as used in the examples and unless otherwise expressly specified, all numbers may be read as if prefaced by the word "about", even if the term does not expressly appear. Also, any numerical range recited herein is intended to include all subranges subsumed therein.

The term "fluorophore" is an art-recognized term used to describe a functional group in a molecule that fluoresces. Fluorophores are well known and used extensively in biological applications such as immunochemistry. Common fluorescent labels include fluorescein and its derivatives, rhodamine and derivatives, dansyl, phycoerythrin, phycocyanin, allophycocyanin, o-phthaldehyde and fluorescamine. See, for example, Hoagland, Handbook of Fluorescent Probes and Research Chemicals, Sixth Ed., Molecular Probes, Eugene, Oreg., 1996, incorporated herein by reference. Examples of additional fluorophores include cascade blue, coumarin and its derivatives, naphthalenes, pyrenes and pyridyloxazole derivatives.

The present invention is a fluorescent sensor capable of unambiguously detecting ozone less sensitive to humidity.

The present invention provides a method of detecting ozone in a sample comprising the steps of 1) contacting the sample with a fluorophore capable of undergoing allylic ether or allylic ester cleavage; and 2) detecting fluorescence in the sample. In the case of biological samples, the pH is preferably adjusted to a suitable biological range, for example about pH 7. For other types of samples, it may be desirable to adjust the pH to higher ranges, such as between about 4-11.

In the present invention, any fluorophore that is dependent upon the presence of a phenoxide or carboxylate group for fluorescence can be used to detect ozone. Accordingly, the term "fluorophore" in the context of the present invention refers to a subset of fluorophores, those that contain a hydroxyl group to which a protecting group can be attached. The bond between the oxygen and the protecting group is cleaved in the presence of ozone, causing the fluorophore to fluoresce. In one embodiment of the present invention, the fluorophore is fluorescein or derivatives of these. Other embodiments of the invention use coumarin or coumarin derivatives. The fluorophore will have a substituted or unsubstituted O-allylic moiety.

"Derivatives" is an art recognized term, and refers to chemical modifications of the compounds such as substitution of halogen for hydrogen at any position in the ring or rings for multi-ring compounds, or the addition of substituents on any of the rings in the compound. Many fluorescein derivatives are known in the art; some are described, for example, in U.S. Pat. Nos. 7,160,732; 6,800,765; 7,087,766; and 5,986,044, each incorporated herein by reference. This list is not meant to be limiting, and is for the purpose of example only.

The fluorophore of the present invention contains a protecting group on the ring-bound oxygen, the protecting group having an allylic functionality. The term "allylic functionality" is used to mean a —$H_2CCR^3$=$CR^1R^2$ termination on the molecule, which can be further substituted, as would be understood by one skilled in the art.

In general, hydroxyl protecting groups are well known in the art. Suitable protecting groups include, for example, alkyl, alkenyl or alkynl groups, including linear or branched embodiments of these, one embodiment being about 1 to about 30 carbons in length, another embodiment being about 1 to about 20 carbons in length, and yet another embodiment being about 1 to about 8 carbons length; cyclic alkyl groups, such as 5 or 6 membered rings, and bicyclic or tricyclic rings; aromatic groups including aryl, alkaryl, and aralkyl groups, and groups having one or more fused rings. Any of the groups may also contain one or more heteratoms such as a halogen, O, N, or S, and can also contain further substitutions thereon.

The term "alkyl" (or "lower alkyl", where lower alkyl means one to six carbons) includes both "unsubstituted alkyls" and "substituted alkyls", the latter of which refers to alkyl moieties having substituents replacing a hydrogen on one or more carbons of the hydrocarbon backbone. Such substituents may include, for example, functional groups such as a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an alkaryl, or an aromatic or heteroaromatic moiety. Such functional groups are also suitable substituents for Y in the formulas described herein (as substitutions on an aryl group), as are other functional groups known in the art and which are commonly used as substitutions on aryl groups. The term "functional group" is art recognized, and the present invention is not limited to those specifically listed.

It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Cycloalkyls may be further substituted with alkyls, alkenyls, alkoxys, alkylthios, aminoalkyls, carbonyl-substituted alkyls, —$CF_3$, —CN, and the like.

In the context of the present invention, any hydroxyl protecting group with allylic functionality can be used, so that the bond between the terminal atom of the protecting group and the oxygen on the fluorophore is susceptible to cleavage by ozone. Determination whether a particular fluorophore with a protecting group can work in the method of the present invention is based on observing the compound on exposure to ozone. If a change in color or fluorescence is detected, the compound is suitable for use as an ozone detector.

One embodiment of the present invention includes the protecting group being an allyl or substituted allyl group.

Another embodiment of the present invention includes the fluorophore that emits light in the ultraviolet or visible spectrum upon contact with ozone. To detect the presence of ozone in a sample, the sample is contacted with the fluorophore of the present invention. If the sample fluoresces (as determined with a UV lamp, laser pen, or other device or by visual observation), then the presence of ozone is confirmed. Visual detection is possible, using the sensors and methods of the present invention, at part-per-million (ppm) or even part-per-billion levels.

The sample containing ozone is optionally adjusted to the desired pH, such as pH 4-11, and then contacted with the fluorophore. If fluorescence is observed, then ozone is present in the sample. Additionally, if fluorescence is detected, this will be an indication that ozone is the only reactive oxygen species present in the sample, as the reaction is specific to ozone.

The amount of fluorophore added to the sample will vary somewhat, based on the level of detection desired and the size of the sample. Detection level and size of sample may be geographically dependent. Typical ozone levels in congested cities will be different than small towns in the Midwest and southwest. Patient respiratory treatment from mild to severe may be different based on ozone thresholds or exceedance of a certain level. In one embodiment of the present invention, the fluorophore can be added in concentrations ranging from about 1 micromolar ($\mu$M) to about 250 $\mu$M, based on a 50 $\mu$L to 5 mL sample size. In another embodiment, the concentration of fluorophore can be added between about 2 $\mu$M to about 200 $\mu$M. In yet another embodiment, the concentration of fluorophore can be added between about 5 $\mu$M and about 20 $\mu$M per any volume of the final solution determined by instrument (e.g., 100-200 $\mu$L with a plate reader used, 0.5-3 mL with a fluorometer used).

Amounts as low as about 2-3 parts per billion (ppb) in a biological or other fluid sample can be detected with the methods of the present invention; in an air sample, amounts as low as 10 ppb can be detected.

Accordingly, the present invention provides an ozone sensor that relies on observation of the fluorescence emission with a simple hand-held long-range UV lamp or laser pen.

The methods of the present invention can be used in numerous scenarios, such as detection of ozone in pharmaceutical samples; biological samples, including cells, blood, plasma, serum, saliva, urine, tears, sweat, cerebrospinal fluid or other tissues; in environmental samples, such as water, air, wastewater; drinking water; water used for preparing compositions for human contact or consumption, such as cosmetic preparations, food and food supplements; and the like. Samples can be gases, liquids or solids.

Fluorescein compounds display fluorescent signal only when the phenolic hydroxy group is deprotonated. Thus, if fluorescein or its derivative were functionalized as a nonfluorescent homoallyl ether, then after reaction with ozone the resulting aldehyde would undergo $\beta$-elimination to yield fluorescent fluorescein and acrolein (See Scheme 1 below). This terminal alkene sensor is specific for ozone because it contains a less electron-rich, isolated (non-conjugated) olefin, which should not react with other ROS to yield a fluorescent signal. Homoallyl ether 4 was designed and synthesized in two steps from commercially available 2',7'-dichlorofluorescein (DCF) in 64% yield. Ozone was bubbled through a solution of homoallyl ether 4 in 95:5 acetone/water and fluorescent compound 7 was obtained in quantitative yield presumably through intermediates 5 and 6.

Scheme 1. Synthesis and mechanistic design of ozone sensor 4.

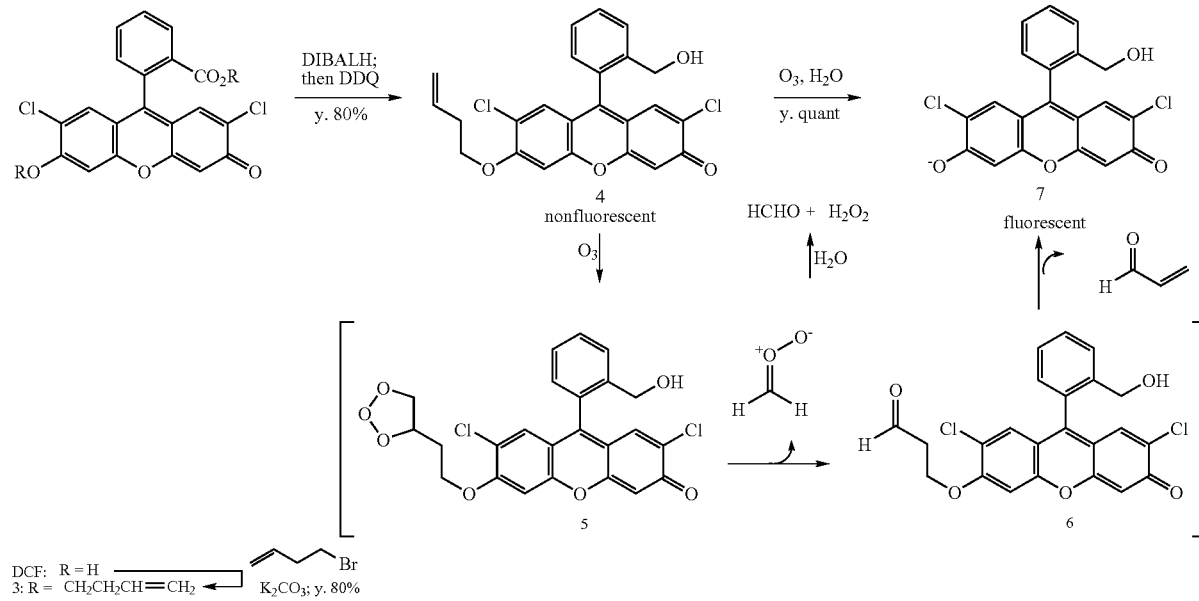

Figure 2A:
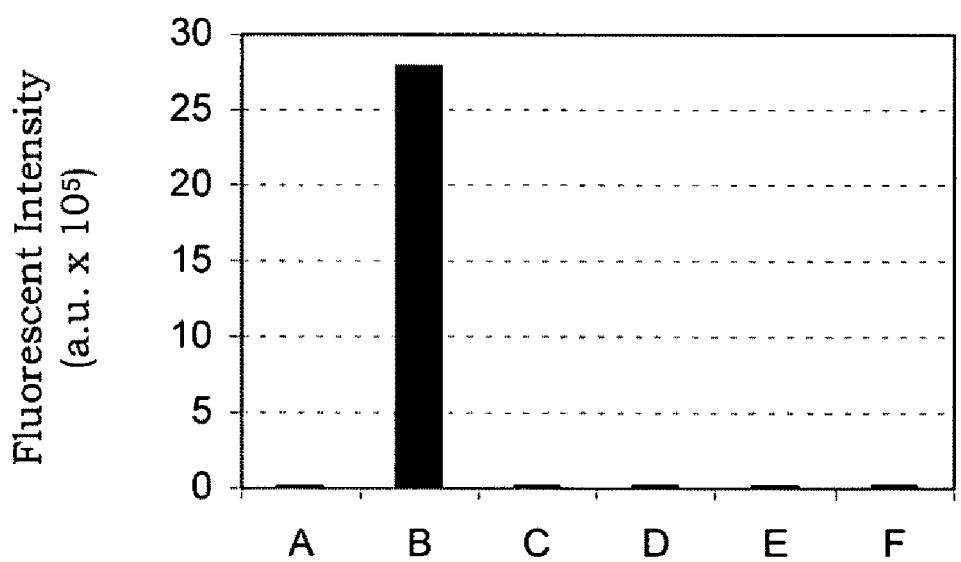
FIGS. 2A-C illustrate Ozone detection in aqueous and biological media.
Figure 2B:
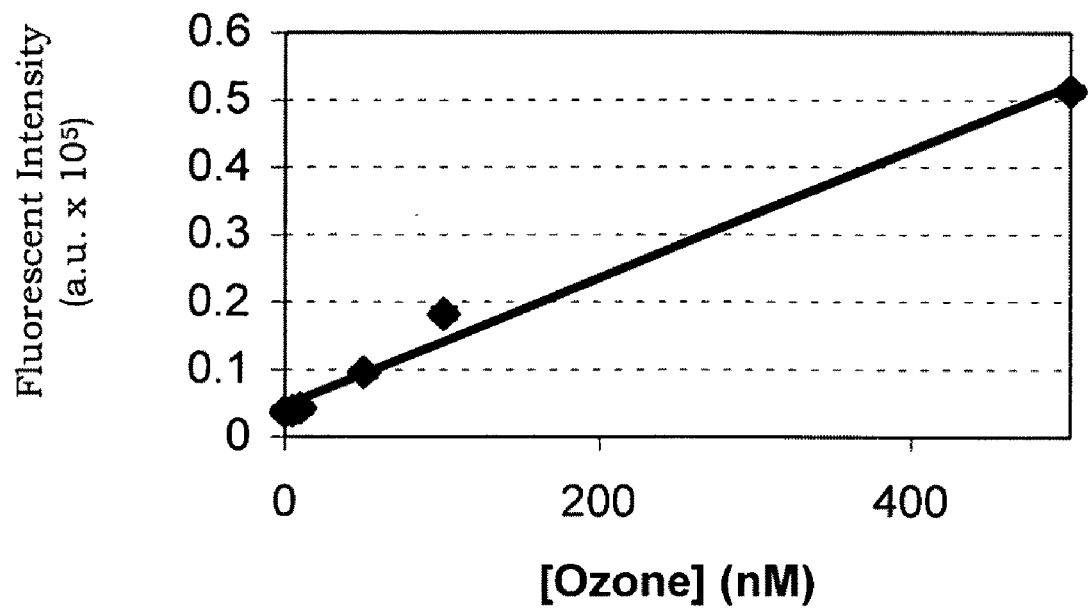
Figure 2C:
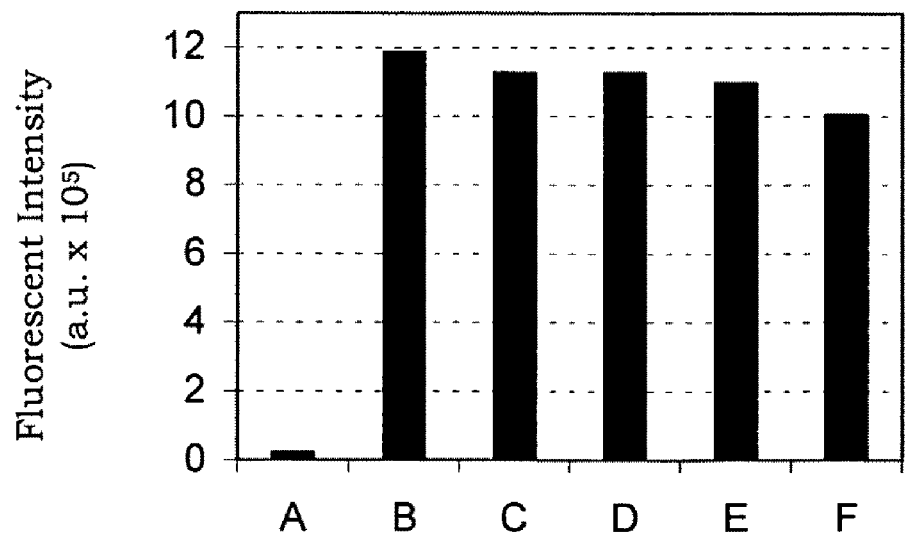

FIGS. 2A-C illustrate ozone detection in aqueous and biological media, wherein the y-axis is fluorescent intensity (a.u.×10⁵) at 523 nm. In all cases, ozone sensor, for example homoallyl ether 4=12.5 µM and ozone was generated by feeding high purity oxygen into a Weisbach T-series ozone generator.

FIG. 2A illustrates ROS specificity, wherein Sample A=no ROS, Sample B=ozone, Sample C=singlet oxygen, Sample D=superoxide, Sample E=hydrogen peroxide, Sample F=hydroxyl radical. The Ozone samples were incubated in 5:95 MeOH/pH 7 buffer at 37° C. for 1 hourafter ozone exposure at 24° C. Singlet oxygen was generated from NaMoO$_4$.2H$_2$O (1.0 mM) and 30% H$_2$O$_2$ (25 mM) in 5:95 MeOH/pH 10 buffer and samples were incubated at 24° C. for 30 min. Superoxide was generated from KO$_2$ (250 µM) and samples were incubated in 5:95 MeOH/pH 7 buffer at 37° C. for 30 min. Samples containing only 30% H$_2$O$_2$ (25 mM) were incubated in 5:95 MeOH/pH 7 buffer at 37° C. for 30 min. Hydroxyl radical was generated from FeSO$_4$.7H$_2$O (250 µM) and 30% H$_2$O$_2$ (250 µM) and samples were incubated in 5:95 MeOH/pH 7 buffer at 37° C. for 30 min.

FIG. 2B is a correlation between fluorescent intensity and ozone in 5:95 MeOH/pH 7 buffer after ten-fold dilution of original samples. The linear correlation is y=0.000900x+ 0.0467; $R^2$=0.987; average standard deviation=0.00844. The intensity continued to be linear up to 12.5 µM.

FIG. 2C illustrates Ozone detection in the presence of antioxidants, wherein Sample A=no ozone, Sample B=ozone only, Sample C=ozone with ascorbic acid (50 µM), Sample D=ozone with glutathione (100 µM), Sample E=ozone with uric acid (100 µM), Sample F=ozone with all antioxidants.

Figure 2D:
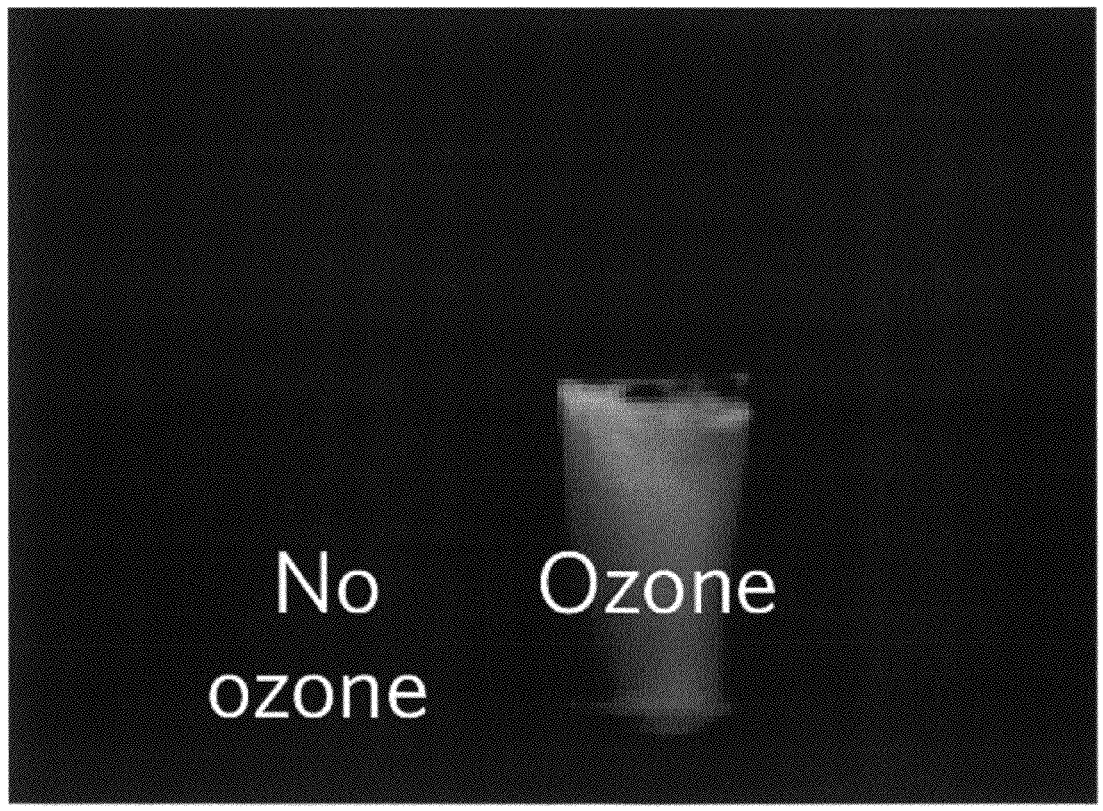
FIG. 2D is a photograph of two samples of nasal fluid with Ozone detected in the right sample as indicated in the bright area.

FIG. 2D illustrates Ozone detection in nasal fluid, wherein Left Sample: 4, no ozone; Right Sample: 4, + ozone.

Figure 2E:
FIG. 2E is a photograph of two samples of human serum with Ozone detected in the right sample as indicated within the white circle.

FIG. 2E illustrates Ozone detection in human serum, wherein Left Sample: 4, no ozone; Right Sample: 4, + ozone.

In order to develop a fluorescent method amenable to both biological and atmospheric detection, pH 7 buffer ([PO$_4^{3-}$]=5 mM) is chosen to perform the conversion of sensor 4, such as homoallyl ether, to fluorescent compound 7. A solution of sensor 4 in 5:95 MeOH/pH 7 buffer at 24° C. is exposed to ozone, incubated at 37° C. for 1 hour to facilitate β-elimination, and formation of fluorescent compound 7 is observed (signal-to-background (S/B)=Sample B (28)/Sample A (0.35)=80) (FIG. 2a). For an ozone detection method in the presence of cells, the ozonolysis reaction is performed in a mixture of pH 7 buffer and RPMI-1640 cell culture media (3:1). This method is compatible with components of the cell culture media (S/B=104; not shown) indicating that this method is amenable for in vitro and in vivo studies.

The present invention was tested against singlet oxygen and superoxide to determine the ROS-specificity. Singlet oxygen was generated in situ from sodium molybdate and hydrogen peroxide and potassium superoxide was used as a source of superoxide. Indigo carmine was used as a positive control to confirm the production of these ROS. No reaction or fluorescent signal was observed with either of these ROS (FIG. 2A). Hydrogen peroxide and hydroxyl radical were also examined because peroxide is a by-product of the aqueous ozonolysis reaction, hydroxyl radical is a product of ozone decomposition in aqueous solution and both are endogenous ROS. For each, no reaction was observed (FIG. 2A). Thus, the present invention is specific for ozone and can be used to unambiguously detect ozone even in the presence of other ROS.

The present invention the sensitivity of our fluorescent method for ozone detection was examined. The fluorescent intensity correlated to the concentration of ozone in the 50 nM-12.5 µM (2.4-600 ppbv) range with S/B of 2.6-310 after 10-fold dilution of the original samples (0-500 nM shown in FIG. 2B). The level of detection is 59 nM (2.9 ppbv; S/B=3) and the level of quantitation is 340 nM (16 ppbv; S/B=10).

One embodiment of the present invention is a biomedical probe to detect ozone. Since ozone is believed to be much too reactive to reach and permeate the epithelial cells, ozone detection in the presence of various antioxidants that are found in the epithelial lining fluid was attempted. Ascorbic acid, glutathione, and uric acid are the most predominant antioxidants present, and as FIG. 2C shows, the present invention is operational even in the presence of physiologically relevant antioxidants. Nasal fluid was tested to more accurately mimic the epithelial lining fluid of the lung. A fluorescent signal was produced (S/B=92; FIG. 2D) indicating that sensor 4 can provide a tool to directly visualize this reactive gas in the study of ozone and the respiratory system.

One embodiment of the present invention utilized sensor 4 to detect ozone in human serum. As FIG. 2E shows, sensor 4 is detects ozone in the presence of other potentially reactive species in serum (S/B=92). This observation proved to be general for this fluorophore scaffold as both dichlorofluorescein (DCF) and fluorescent compound 7 behaved in a similar manner in serum (not shown). One possible explanation may be due to the small Stokes shift that is found in fluorescein and its derivatives, which makes these fluorophores more prone to influences of scattering and interference.

Figure 3A:
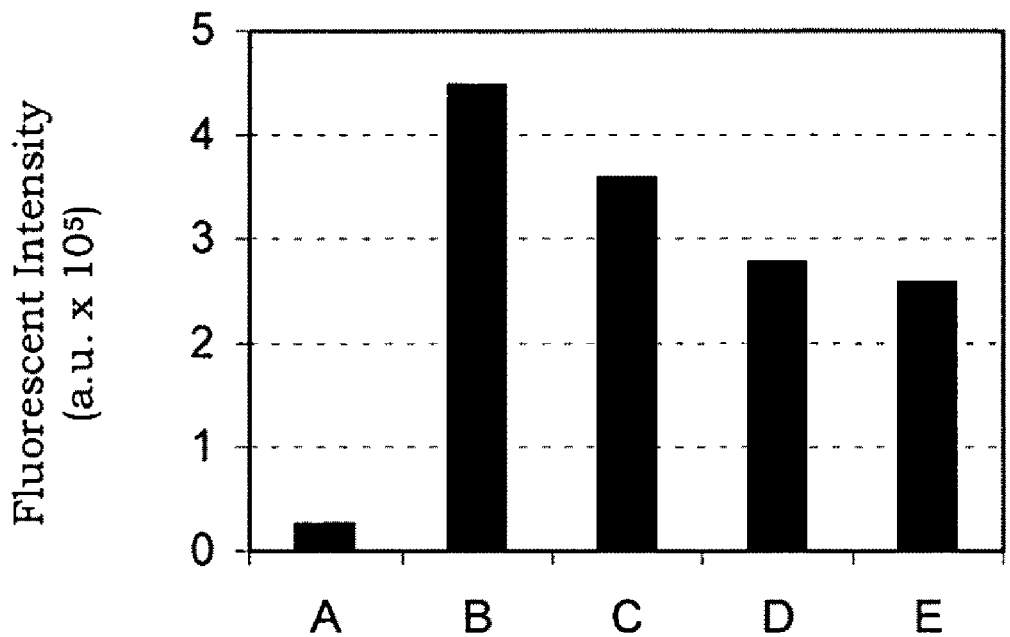
FIGS. 3A-B illustrate Ozone detection in ambient air.
Figure 3B:
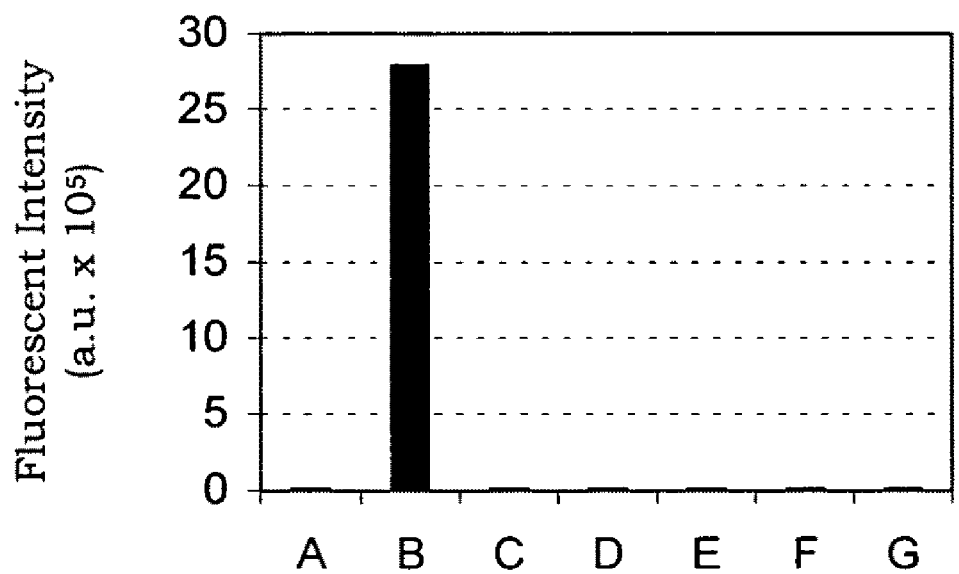

FIGS. 3A-B illustrates ozone detection in ambient air. In both graphs, the y-axis is fluorescent intensity (a. u.$\times 10^5$) at 523 nm. In all cases, sensor 4=12.5 µM and all ozone assays were performed in 5:95 MeOH/pH 7 buffer. Solutions of senor 4 in 5:95 MeOH/pH 7 buffer were prepared and exposed to ambient air in various locations throughout a city on a hot, sunny day (~32° C.) for 8 hours. A negative control was prepared in the same manner but incubated at 37° C. in a closed vial for 8 hours.

In FIG. 3A, Ozone detection occurred in outdoor air for 8 hours. A=negative control, B-E=outdoor air samples at various locations.

FIG. 3B illustrates Ozone specificity against other air pollutants: Sample A=no additive, Sample B=ozone, Sample C=$HNO_3$, Sample D=$H_2SO_4$, Sample E=Pb, Sample F=Pd, Sample G=Pt. [Acid]=250 µM. [Metal]=100 nM. The acid samples were incubated in 5:95 MeOH/pure water for 30 minutes at 37° C. The metal samples were incubated in 5:95 MeOH/pH 7 buffer for 30 minutes at 37° C.

Ozone detection was observed with S/B values of 10-17 (FIG. 3A), which correlates to 13-22 ppb based on linear regression. A number of other pollutants were screened to ensure that ozone was selectively detected. Nitrogen dioxide and sulfur dioxide convert to their corresponding acids in aqueous solution so nitric acid and sulfuric acid were screened. Lead, palladium and platinum, which are known pollutants emitted from automobiles, were also screened. As FIG. 3B shows, none of these species C-G produced a fluorescent signal. In addition to the specificity, the sensing method of the present invention performs in aqueous media and will not be impacted by humidity of any amounts up to 100% humidity. Thus, senor 4 may be used as a sensitive probe for ozone in the atmosphere.

Figure 3C:
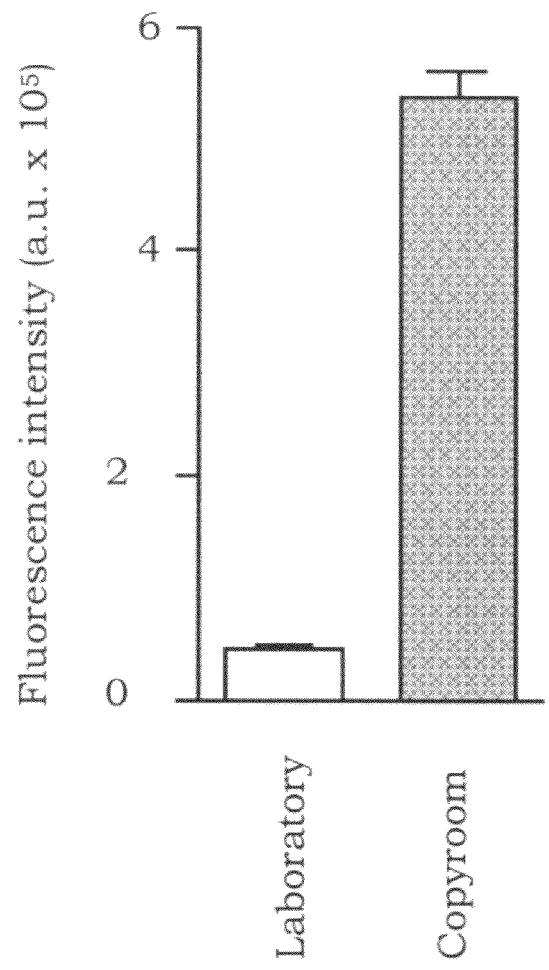
FIG. 3C-D illustrate fluorescence emission of compound 7.
Figure 3D:
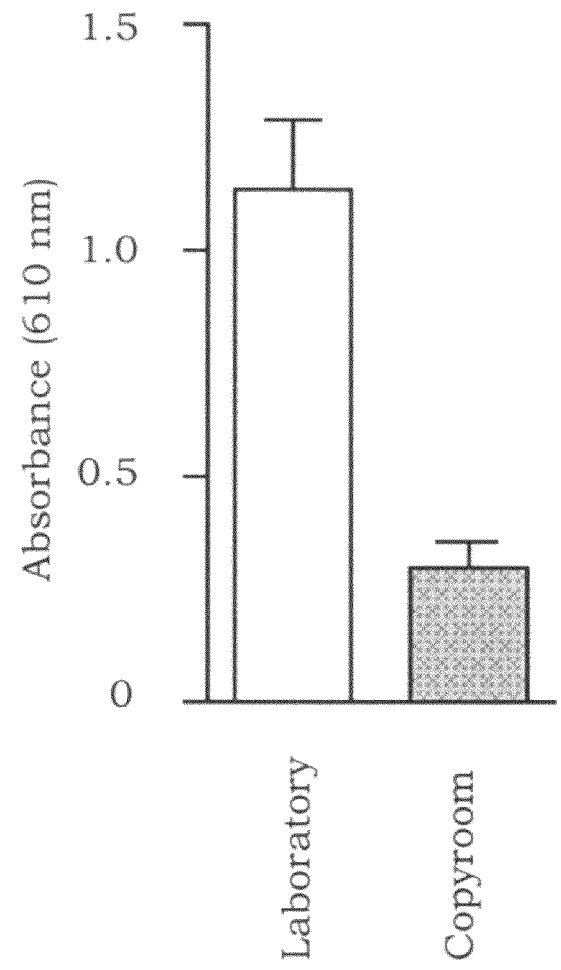

One embodiment of the present invention can be a badge that contains compound 4 that may be worn by patients so their total ozone exposure can be continuously measured through the day. A proof-of-principle experiment was conducted with compound 4 and compound 1 as a comparative. A solution of compound 4 (500 nmol) in dimethylsulfoxide (DMSO) was absorbed on a piece of adsorbent paper and allowed to dry. The paper strips were stored in an office room that had two photocopiers and two laser printers. After eight hours, the paper strips were removed and placed in a vial that contained oH 7 buffer to elute the dyes. FIG. 3C and the fluorescent emission of compound 7 shows that the paper strip that contained compound 4 displayed 0.95 nmol of compound 7 being generated, which indicates that at least 0.95 nmol of ozone was exposed to the strip over eight hours. FIG. 3D shows the paper strip that contained compound 1 displayed a 77% decrease in absorbance at 610 nm, which correlates to the consumption of 387 nmol of compound 1. The deviation in these values is presumably because of photobleaching and the lack of specificity of compound 1 towards various ROS, including singlet oxygen.

The present invention is a specific and robust fluorescent sensor for ozone. This method is capable of fluorescently detecting ozone in biological samples, including nasal fluid and serum, and in ambient air. The key benefits of method of the present invention are resistance to cleavage by other oxidants other than ozone, specificity against other known atmospheric pollutants, water compatibility and ease of measurement, thereby eliminating false positions. This method will aid in understanding ozone's role in human health and the atmosphere. Additionally, due to the simplicity of the method, an inexpensive hand-held fluorometer can be adapted to implement the method for use by the general public to monitor their exposure to ozone at home, especially for those who suffer from respiratory diseases.

Methods Summary

Ozone detection method. Solutions of compound 4 ($[4]_{final}$=12.5 µM) in 5:95 MeOH/pH 7 buffer ($[PO_4^{3-}]$=5 mM) solution (4.0 mL) were prepared, and the samples were exposed to ozone at 24° C. followed by 1 hour incubation at 37° C. before fluorescence measurement (except for the ambient air experiments). The concentration of ozone was 5 µM for these studies. Fluorescence spectra were recorded in a 1×1-cm disposable cuvette on a Jobin Yvon FluoroMax-3 spectrometer under the control of a Windows-based PC running FluorEssence software. The samples were excited at 497 nm and the emission intensities were collected at 523 nm. All spectra were corrected for emission intensity using the manufacturer supplied photomultiplier curves.

Ozone detection in ambient air were demonstrated. Solutions of senor 4 ($[4]_{final}$=12.5 µM) in 5:95 MeOH/pH 7 buffer ($[PO_4^{3-}]$=5 mM) solution (4.0 mL) were prepared, and the samples were placed in high traffic outdoor areas for 8 hours. The samples were not exposed directly to sunlight. A negative control was prepared in the same manner but incubated at 37° C. in a closed vial for 8 hours. Following the 8 hour incubation period, the fluorescence of each sample was measured.

Ozone detection in live human epithelial cells were demonstrated. Human bronchial epithelial cells (BEAS-2B) (American Type Culture Collectin) were grown in LHC-9 medium (Invitrogen) on glass-bottomed Petri dishes (MatTek) precoated with 0.01 mg ml$^{-1}$ of human fibronectin (Invitrogen), 0.029 mg ml$^{-1}$ Vitrogen 100 (Cohesion) and 0.01 mg ml$^{-1}$ bovine serum albumin (Invitrogen) in LHC-9 medium. Immediately prior to imaging, cells were rinsed with Hank's balanced salt solution, which contained calcium and magnesium, and placed inside a temperature-controlled, airtight environmental chamber and maintained at 37° C. and 5% $CO_2$. Images were obtained using a Nikon TE2000E-PFS (Perfect focus system) microscope equipped with a 49× oil-immersion objective (Nikon, CFI PlanFluor, NA 1.3) and a fluorescien isothiocyanate longpass filter set (Chroma), a Q-Imaging SRV CCD camera (Q-imaging) and MetaMorph software (Molecular Devices). The motorized XYZ stage used was made by ASA (Eugege). Baseline images were collected before the addition of compound 8 and time-lapsed images obtained at 30 second intervals after the addition of compound 8 (250 nM). Once stage baseline had been achieved, multiple washes were carried out and the media replaced. The cells were then exposed to ozone (~2.1 ppm) and monitored every 30 seconds for 15 minutes. Ozone was generated from medical grade oxygen (Valley Gas) via a model V1-0 ultraviolet ozonator (OREC) and analyzed with a Dasibi (Glendale) direct-reading instrument. Ozone concentrations were maintained by adjusting both the intensity of the ultraviolet light and the flow rate of oxygen. For each experiment, images were collected from six stages, with a minimum of five cells per position (a minimum of 30 cells per equipment).

Experimental Background

Ozone was generated by feeding high purity oxygen into a Weisbach T-series ozone generator. RPMI-1640 medium (without L-glutamine and phenol red) is a product of HyClone® and was used as received. Human pleural fluid was purchased from Lee Biosolutions and used as received. Human serum (off-the-clot, type AB) was purchased from PAA Laboratories, Inc. and used as received. Kimwipes° is a product of Kimberly-Clark. Buffers were purchased from J. T. Baker (pH 7, catalog number 5608-01) and used after dilution with ARISTAR® ULTRA Water.

All reactions were carried out under a nitrogen atmosphere with dry, freshly distilled solvents under anhydrous conditions, unless otherwise noted. Tetrahydrofuran (THF) was distilled from sodium-benzophenone, and methylene chloride ($CH_2Cl_2$) was distilled from calcium hydride. Yields refer to chromatographically and spectroscopically ($^1$H NMR) homogenous materials, unless otherwise stated.

All reactions were monitored by thin-layer chromatography (TLC) carried out on 0.25-mm EMD silica gel plates (60E-254) using UV-light (254 nm). TSI silica gel (230-400 mesh) was used for flash column chromatography.

NMR spectra were recorded on AM300 (Bruker) instruments and calibrated using a solvent peak as an internal reference. The following abbreviations are used to indicate the multiplicities: s, singlet; d, doublet; t, triplet; q, quartet; m, multiplet; br, broad. Mass spectra were obtained from a Micromass Autospec double focusing instrument.

Experimental Section

Preparation of compound 3. A 100-mL round bottom flask was charged with 2',7'-dichlorofluorescein (2.4 g, 5.89 mmol), DMF (20 mL), $K_2CO_3$ (2.5 g, 17.7 mmol) and 4-bromobutene (1.8 mL, 17.7 mmol) at 24° C. The reaction mixture was stirred at 70° C. for 8 hours and then poured into 750 mL water. The resulting precipitate was washed with water and dried in vacuo to yield compound 4 as a red-orange solid (2.4 g; 80%).

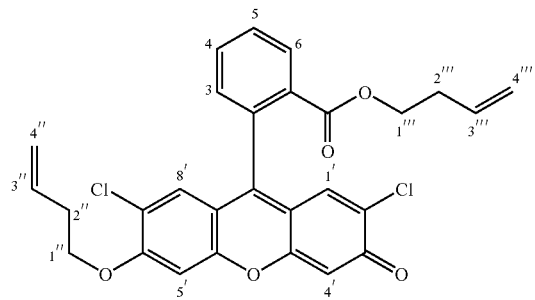 [SMILES: C=CCCOC(=O)c1ccccc1-c1c2cc(Cl)c(=O)cc-2oc2cc(OCCC=C)c(Cl)cc12]

Data for compound 3: mp=184-185° C.; $R_f$=0.34 (70% EtOAc in hexanes); IR (KBr pellet): 1725 (C=O), 1593, 1521, 1278, 997 cm$^{-1}$; 1H NMR (300 MHz, CDCl$_3$, 293K): δ 8.32 (dd, J=7.5, 1.2 Hz, 6-H), 7.82-7.68 (m, 2H, 4-H, 5-H), 7.26-7.30 (br d, J=7.5 Hz, 1H, 3-H), 7.04 (s, 1H, Ar), 7.03 (s, 1H, Ar), 6.95 (m, 1H, Ar), 6.60 (s, 1H, Ar), 5.93 (ddt, J=16.9, 10.3, 6.6 Hz, 1H, 3'''-H), 5.60 (ddt, J=16.5, 9.9, 6.6 Hz, 1H, 3''-H), 5.24 (ddt, J=17.1, 3.3, 1.5 Hz, 1H, 4'''-H$_{trans}$), 5.18 (ddt, J=10.2, 3.3, 1.5 Hz, 1H, 4'''-H$_{cis}$), 5.02 (ddt, J=17.1, 3.3, 1.5 Hz, 1H, 4''-H$_{trans}$), 4.97 (ddt, J=10.2, 3.3, 1.5 Hz, 1H, 4''-H$_{cis}$), 4.20 (t, J=6.7 Hz, 2H, 1'''-H), 4.13 (t, J=6.7 Hz, 2H, 1''-H), 2.68 (q, J=6.6 Hz, 2H, 2'''-H), 2.23 (q, J=6.6 Hz, 2H, 2''-H); $^{13}$C NMR (75 MHz, CDCl$_3$, 293K): δ 177.7, 169.4, 158.6, 157.8, 152.5, 149.8, 135.2, 133.5, 133.3, 133.2, 133.1, 131.6, 130.4, 130.3, 130.2, 128.0, 127.4, 120.5, 118.1, 117.6, 117.4, 114.9, 105.7, 100.7, 69.2, 64.5, 33.0, 32.6; HRMS (ESI) m/z calcd for $C_{28}H_{23}Cl_2O_5$ [M+H]$^+$ 509.0923, found 509.0876.

Preparation of compound 4. A solution of compound 3 (200 mg, 0.392 mmol) in $CH_2Cl_2$ (1.32 mL) was treated with DIBALH (1.4 mL, 1.0 M in hexanes, 1.4 mmol) dropwise over 15 minutes at −78° C. under a nitrogen atmosphere. The mixture was stirred for 5 minutes at the same temperature and then was warmed to 24° C. After 2 h, the reaction mixture was quenched with saturated aqueous NH$_4$Cl (700 μL) and diluted with Et$_2$O (2.9 mL) at 0° C. DDQ (2.50 g, 11.0 mmol) was then added to the mixture at 0° C. After stirring 15 min, the mixture was filtered through Celite® and washed with Et$_2$O. The filtrate was dried over Na$_2$SO$_4$ and the solvents were evaporated under reduced pressure. Silica gel flash chromatography of the residue (5 to 10% EtOAc in hexanes) afforded compound 2 as a light orange solid (134 mg, 80%).

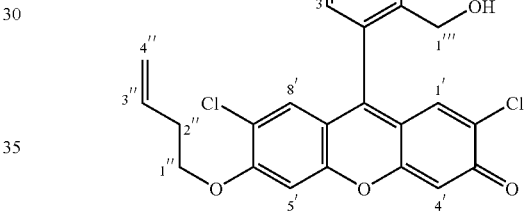

Data for compound 4: mp=167-168° C.; $R_f$=0.69 (50% EtOAc in hexanes); IR (KBr pellet): 3387 (br O—H), 3080, 2925, 2857, 1608, 1480, 1416, 1035 cm$^{-1}$; $^1$H NMR (300 MHz, CDCl$_3$, 293K): δ 7.39-7.45 (m, 2H, Ar), 7.28-7.30 (m, 1H, Ar), 6.91 (s, 1H, Ar), 6.90 (s, 1H, Ar), 6.88 (s, 1H, Ar), 6.85 (s, 1H, Ar), 6.76 (s, 1H, Ar), 5.94 (ddt, J=17.1, 10.5, 6.6 Hz, 1H, 3''-H), 5.26 (ddt, J=17.1, 3.3, 1.5 Hz, 1H, 4''-H$_{trans}$), 5.17 (ddt, J=10.2, 3.3, 1.5 Hz, 1H, 4''-H$_{cis}$), 5.34 (s, 2H, 1'''-H), 4.11 (t, J=6.7 Hz, 2H, 1''-H), 2.63 (ddd, J=6.6, 6.6, 1.5 Hz, 2H, 2''-H); $^{13}$C NMR (75 MHz, CDCl$_3$, 293K): δ 154.9, 151.9, 150.1, 149.6, 143.9, 138.6, 133.8, 129.5, 128.7, 128.6, 128.3, 123.7, 121.0, 118.2, 118.1, 117.5, 117.1, 115.5, 103.6, 101.1, 83.1, 72.3, 68.6, 33.2; HRMS (ESI) m/z calcd for $C_{24}H_{19}Cl_2O_4$ [M+H]$^+$ 441.0660, found 441.0683.

Preparation of compound 7. A solution of compound 4 (34.2 mg, 0.0775 mmol) was prepared in 95:5 acetone/water (585 μL total, 0.15 mM). The solution was cooled to 0° C. and ozone was bubbled through the sample for 2 min. Following ozonolysis, a small amount of KI (<5 mg) was added and the solution was stirred at 24° C. for 1 min. TLC analysis (50% EtOAc in hexanes) indicated complete conversion to compound 7. Details of the spectroscopic, absorbance and fluorescence properties of compound 7 can be found in Song, F.; Garner, A. L.; Koide, K. *J. Am. Chem. Soc.* 2007, 129, 12354, and $^1$Koide, K.; Song, F.; de Groh, E. D.; Garner, A. L.; Mitchell, V. D.; Davidson, L. A.; Hukriede, N. A. *ChemBioChem* 2008, 9, 214, both incorporated herein by reference.

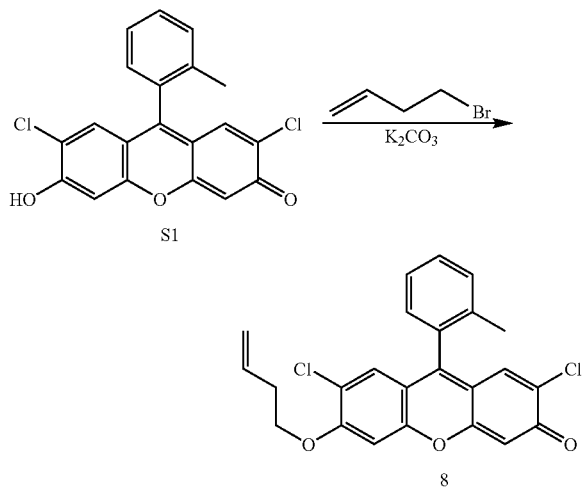

Preparation of compound 8. 4-Bromo-1-butene (168 μL, 1.7 mmol) and $K_2CO_3$ (263 mg, 1.9 mmol) were added to a solution of compound S1 (176 mg, 0.47 mmol) in DMF (2 mL), and the resulting mixture was heated at 80° C. under $N_2$ for 36 h. The reaction mixture was then poured to $H_2O$ (30 mL) and extracted with EtOAc (2×30 mL). The combined organic layers were washed with $H_2O$ (50 mL) and brine (50 mL), dried over $Na_2SO_4$, and concentrated under reduced pressure. The residue was purified by flash chromatography (10 to 40% EtOAc in hexanes) on silica gel (60 mL) to afford compound 8 (46 mg, 23% yield) as an orange solid.

Data for compound 8: $R_f$=0.34 (50% EtOAc in hexanes); mp=142-143° C.; IR (KBr): 2923, 2853, 1637 (C=O), 1608, 1514, 1435, 1336, 1280, 1000, 916, 834 cm$^{-1}$; $^1$H NMR (300 MHz, 293K, CDCl$_3$) δ 7.56-7.40 (m, 3H), 7.16 (d, J=9.6 Hz, 1H), 7.14 (s, 1H), 7.06 (s, 1H), 7.04 (s, 1H), 6.60 (s, 1H), 5.93 (ddt, J=17.1, 10.5, 6.6 Hz, 1H), 5.25 (ddt, J=17.1, 3.3, 1.5 Hz, 1H), 5.19 (ddt, J=10.5, 3.3, 1.5 Hz, 1H), 4.23 (t, J=6.6 Hz, 2H), 2.69 (tdd, J=6.6, 6.6, 1.5 Hz, 2H), 2.09 (s, 3H); $^{13}$C NMR (75 MHz, 293K, CDCl$_3$) δ 177.8, 158.9, 157.8, 152.8, 148.8, 136.0, 135.6, 133.1, 131.5, 131.0, 130.1, 129.0, 128.4, 127.6, 126.5, 120.7, 118.3, 118.1, 114.3, 105.8, 100.7, 69.3, 33.0, 19.7; HRMS (EI+) calcd. for $C_{24}H_{18}Cl_2O_3$ [M$^+$] 424.0633, found 424.0644.

Preparation of Parent Stock Solutions.

| Entry | Reagent | Quantity | Solvent (10 mL) | Conc. of stock solution |
|---|---|---|---|---|
| A | Compound 4 | 44.1 mg (0.10 mmol) | DMSO | 10.0 mM |
| B | Indigo Carmine | 46.6 mg (0.10 mmol) | DMSO | 10.0 mM |
| C | NaMoO$_4$•2 H$_2$O | 206.0 mg (1.00 mmol) | pH 10 buffer | 100 mM |
| D | KO$_2$ | 71.1 mg (1.00 mmol) | DMSO | 100 mM |
| E | FeSO$_4$•7 H$_2$O | 278.0 mg (1.00 mmol) | pH 7 buffer | 100 mM |
| F | L-Ascorbic acid sodium salt | 19.8 mg (0.10 mmol) | pH 7 buffer | 10.0 mM |
| G | Glutathione, reduced | 30.7 mg (0.10 mmol) | pH 7 buffer | 10.0 mM |
| H | Uric acid | 16.8 mg (0.10 mmol) | pH 7 buffer | 10.0 mM |
| I | Pb(NO$_3$)$_2$ | 16.6 mg (50 μmol) | MeOH | 5.0 mM |
| J | PdCl$_2$ | 9.0 mg (50 μmol) | 3:1 Brine/MeOH | 5.0 mM |
| K | PtCl$_2$ | 13.3 mg (50 μmol) | DMSO | 5.0 mM |

Notes:
(1) All the solutions were stored at 24° C.
(2) Solution A was stored in the dark as a precautionary measure.
(3) All solutions for testing the ROS specificity were prepared and used immediately.
(4) All solutions for testing detection in the presence of antioxidants were prepared and used immediately.

UV-visible spectroscopy. Absorption spectra were acquired in a 1×1-cm quartz cuvette (Spectrocell Inc.; product number RF-2010) on a Perkin Elmer Lambda 19 UV-Visible spectrometer under the control of a Windows-based PC running the manufacturer's supplied software.

Fluorescence spectroscopy. Fluorescence spectra were recorded in a 1×1-cm disposable cuvette (VWR; catalog number 58017-880) on a Jobin Yvon FluoroMax-3 spectrometer under the control of a Windows-based PC running FluorEssence software. The samples were excited at 497 nm and the emission intensities were collected at 523 nm. All spectra were corrected for emission intensity using the manufacturer supplied photomultiplier curves.

FIGS. 4A-H illustrate absorbance and fluorescence emission of compounds 4, 7, 8, and S1, wherein fluorescence and emission spectra were measured in 0.1% DMSO in pH 7 buffer. FIG. 4A is absorbance spectrum of compound 4. FIG. 4B is Emission spectrum of compound 4. FIG. 4C is Absorbance spectrum of compound 7. FIG. 4D is Emission spectrum of compound 7. FIG. 4E is Absorbance spectrum of compound 8. FIG. 4F is Emission spectrum of compound 8. FIG. 4G is Absorbance spectrum of compound S1. FIG. 4H is Emission spectrum of compound S1.

Figure 4I:
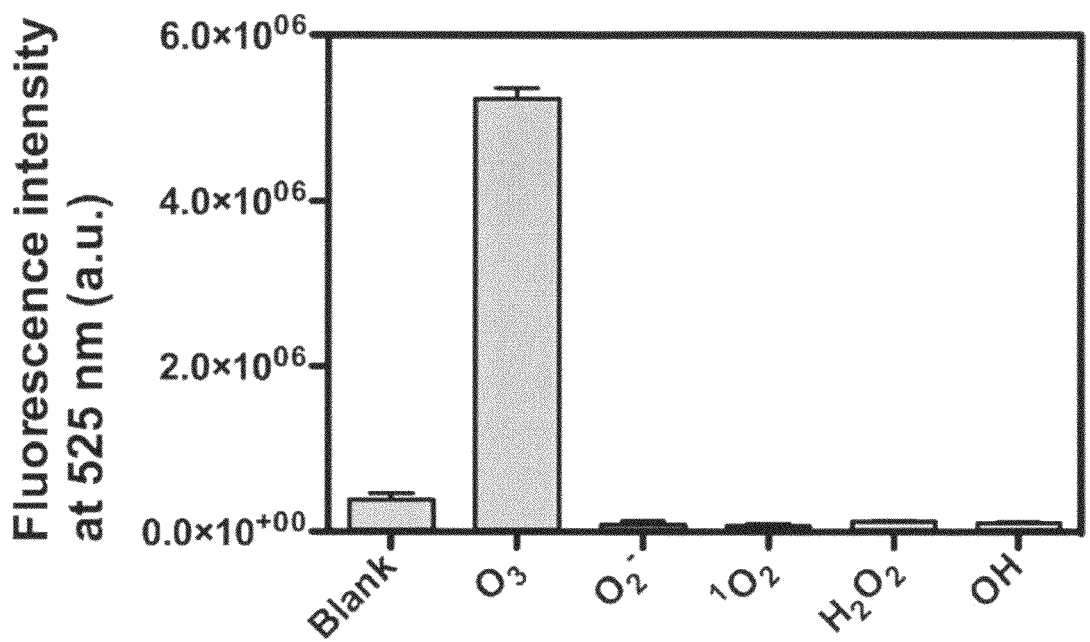
FIG. 4I is the ROS with compound 8.
Figure 4J:
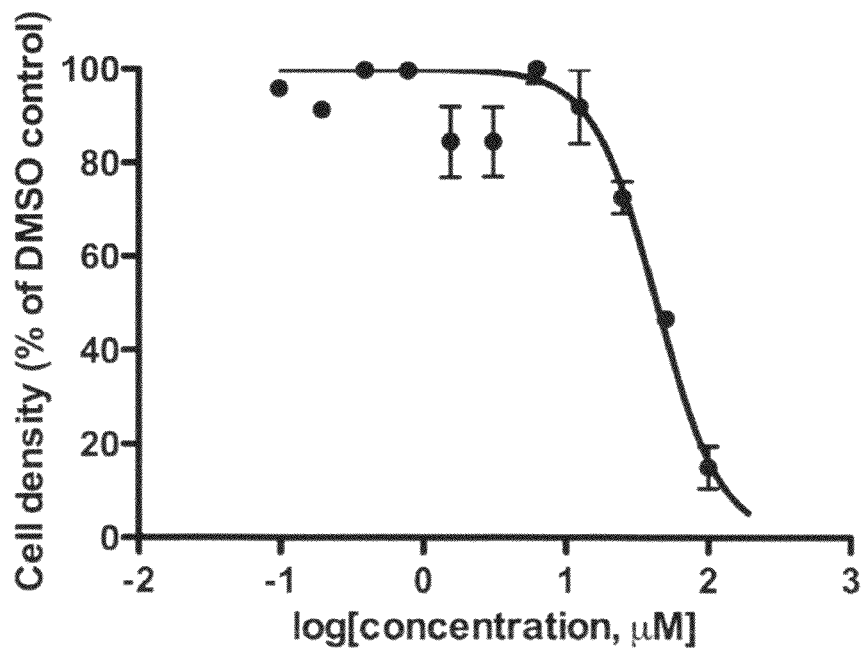
FIG. 4J is the cytotoxicity of compound 8 against HeLa cells seeds at a density of 2000 cells/well is a 96-well plate.

FIG. 4I is the ROS with compound 8. The experiment was performed in duplicate. Error bars were determined from the calculated mean and standard deviation (Prism 5.0a, GraphPad Software, Inc.). FIG. 4J is the cytotoxicity of compound 8 against HeLa cells seeds at a density of 2000 cells/well is a 96-well plate. Concentrations of compound 8 ranged from 10 nM to 200 μM. The assay was performed for 3 days, and the relative cell density was determined by an MTS assay (Promega CellTiter 96® AQueous Non-Radioactive Cell Proliferation Assay). The 10$_{50}$ of compound 8 was found to be 43 μM.

Relative Quantum Yields. To determine quantum yields relative to fluorescein, a stock solution of compound 4 was prepared in DMSO (1 mM) and diluted in phosphate buffer (pH=7.0) to OD$_{490}$=0.09. The samples were excited at 490 nm and the integrated emission spectra were compared. The quantum yields of all compounds were referenced to fluorescein in 0.1 N NaOH (Φ=0.95). The quantum yield for compound 4 was calculated as 0.00132

Mechanistic Rationale of Ozone Specificity.

Figure 5A:
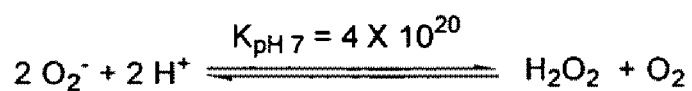
FIGS. 5A-C illustrate mechanistic rationale of fluorescence turn-on specificity for ozone.
Figure 5B:
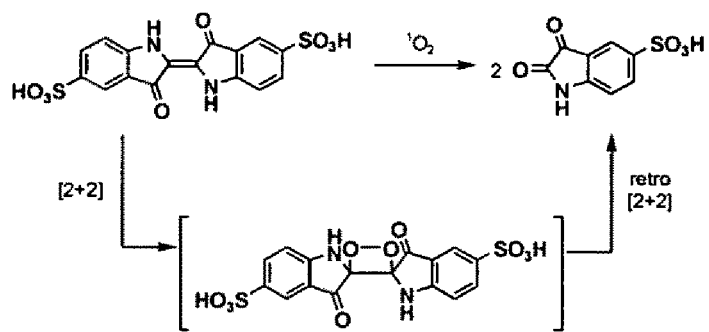

Mechanistic rationale of fluorescence turn-on specificity for ozone: FIG. 5A: Superoxide disproportionate in pH 7 buffer; FIG. 5B: The reaction of indigo carmine with singlet oxygen; and FIG. 5C: The reaction of compound 4 with singlet oxygen.

Figure 5C:
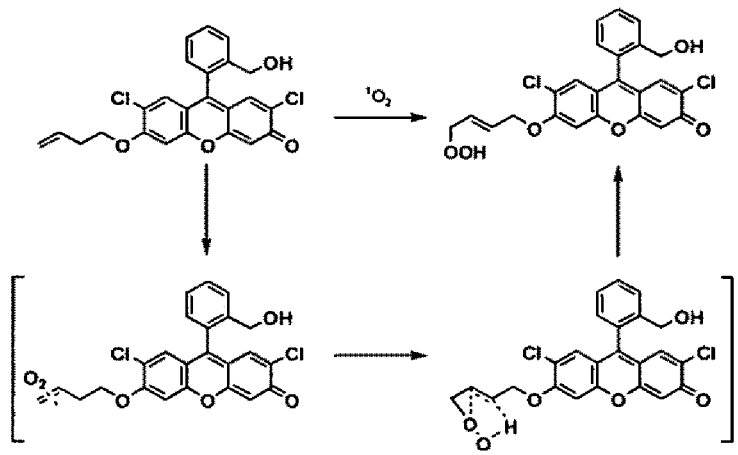

Reactivity of indigo carmine and compound 4. Indigo carmine would be expected to be more reactive towards ozone from a frontier molecular orbital view due to the presence of its α,β-unsaturated ketone moiety (higher HOMO, lower LUMO); however, this moiety also makes it more reactive toward other ROS. With respect to compound 4, because the dominant characteristic of superoxide is to act as a strong Brönsted base, it would likely deprotonate the primary hydroxy group, which would not produce a fluorescence signal. In addition, the disproportionation of superoxide in pH 7 buffer is extremely fast precluding reaction with compound 4 (FIG. 5A). Finally, in the presence of singlet oxygen, because indigo carmine does not contain allylic hydrogens, it will undergo [2+2] cycloaddition followed by a retro-[2+2] cycloaddition to yield isatin sulfonic acid (FIG. 5B). Compound 4, however, contains allylic hydrogens and will undergo an ene-type reaction, which again will not produce a fluorescence signal (FIG. 5C). Other ROS may react with compound 4, but in each case a fluorescence signal will not be produced.

ROS Specificity:

For each ROS experiment, triplicate replicas were performed.

Ozone: Solution A (5.0 μL, [compound 4 or compound 8]$_{final}$=12.5 μM) was added to a mixture of MeOH/pH 7 buffer ([$PO_4^{3-}$]=5 mM) (5:95) (4.0 mL), and the samples were exposed to ozone (~5 μM) at 24° C. followed by 1 hour incubation at 37° C. before fluorescence measurement.

Singlet oxygen: Solution A (5.0 μL, [compound 4 or compound 8]$_{final}$=12.5 μM), solution C (40.0 μL, [$NaMoO_4 \cdot 2H_2O$]$_{final}$=1.0 mM) and $H_2O_2$ (10 μL, [$H_2O_2$]$_{final}$=25.0 mM) were added to a mixture of MeOH/pH 10 buffer (5:95) (4.0 mL), and the samples were incubated for 30 minutes at 24° C.

Superoxide: Solution A (5.0 μL, [compound 4 or compound 8]$_{final}$=12.5 μM) and solution D (10.0 μL, [$KO_2$]$_{final}$=250 μM) were added to a mixture of MeOH/pH 7 buffer solution (5:95) (4.0 mL), and the samples were incubated for 30 minutes at 37° C.

Hydrogen peroxide: Solution A (5.0 μL, [compound 4 or compound 8]$_{final}$=12.5 μM) and 30% $H_2O_2$ (10 μL, [$H_2O_2$]$_{final}$=25.0 mM) were added to a mixture of MeOH/pH 7 buffer solution (5:95) (4.0 mL), and the samples were incubated for 30 minutes at 37° C.

Hydroxyl radical: Solution A (5.0 μL, [compound 4 or compound 8]$_{final}$=12.5 μM), solution E (10.0 μL, [$FeSO_4 \cdot 7H_2O$]$_{final}$=250 μM) and 30% $H_2O_2$ ([$H_2O_2$]$_{final}$=250 μM) were added to a mixture of MeOH/pH 7 buffer solution (5:95) (4.0 mL), and the samples were incubated for 30 minutes at 37° C.

Figure 6A:
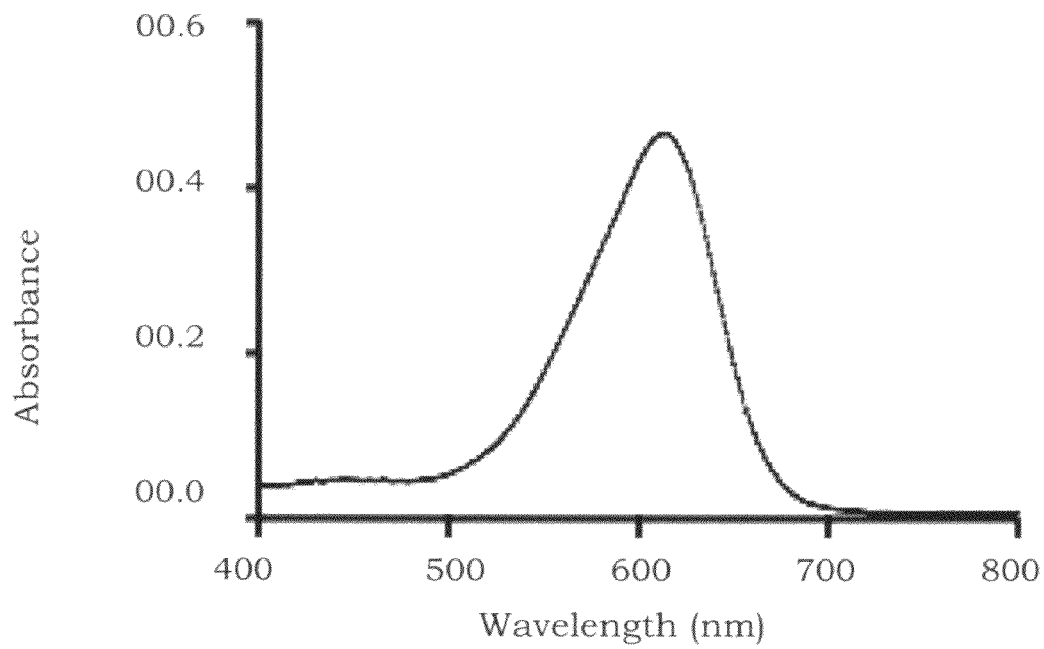
FIG. 6A-B illustrates Indigo carmine with various ROS.
Figure 6B:
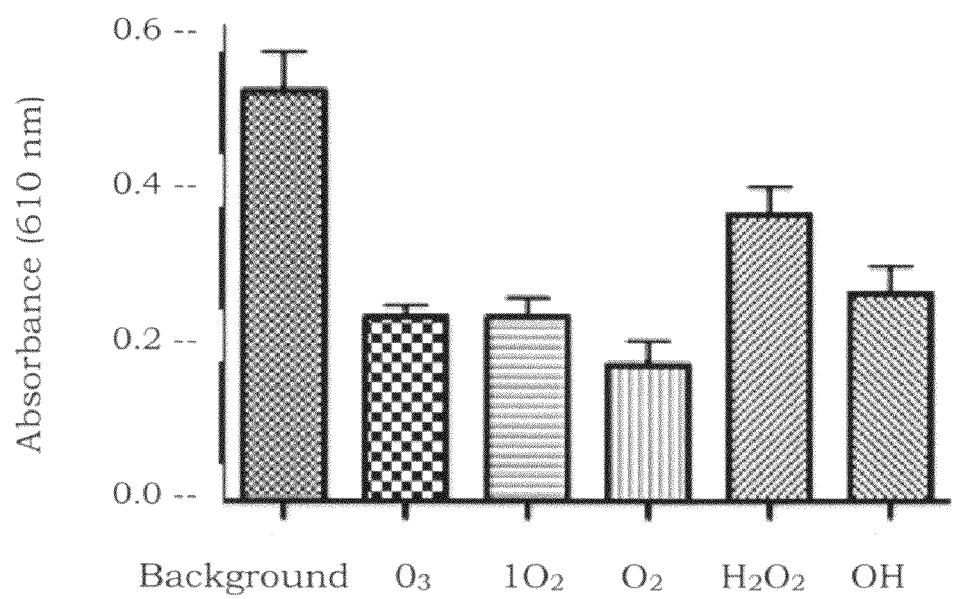

Indigo carmine with various ROS. The ROS experiments described above were repeated using indigo carmine (Solution B, [Indigo Carmine]$_{final}$=12.5 μM in all cases) in triplicate. The data are shown in FIG. 6A-B indicates that Indigo carmine reacts with nearly all ROS with a 11-70% decrease in absorbance at 610 nm. FIG. 6A is the Absorbance spectrum of indigo carmine. FIG. 6B is the ROS with indigo carmine. Error bars were determined from the calculated mean and standard deviation (Prism 5.0a, GraphPad Software, Inc.).

Time-dependence of the conversion of compound 4 to compound 7 in buffer. Solution A ([compound 4]$_{final}$=12.5 μM) was added to a mixture of MeOH/pH 7 buffer ([$PO_4^{3-}$]=5 mM) (5:95) (4.0 mL), and the sample was exposed to ozone (~5 μM) at 24° C. followed by incubation at 37° C. Aliquots of the reaction mixture were taken out at various times for fluorescence measurement (FIG. S6). The conversion of compound 4 to compound 7 requires 60 minutes for completion (presumably the β-elimination is the rate determining step because the formation and fragmentation of molozonides are extremely rapid), but 10-15 minutes is sufficient to observe fluorescence signal.

Figure 7:
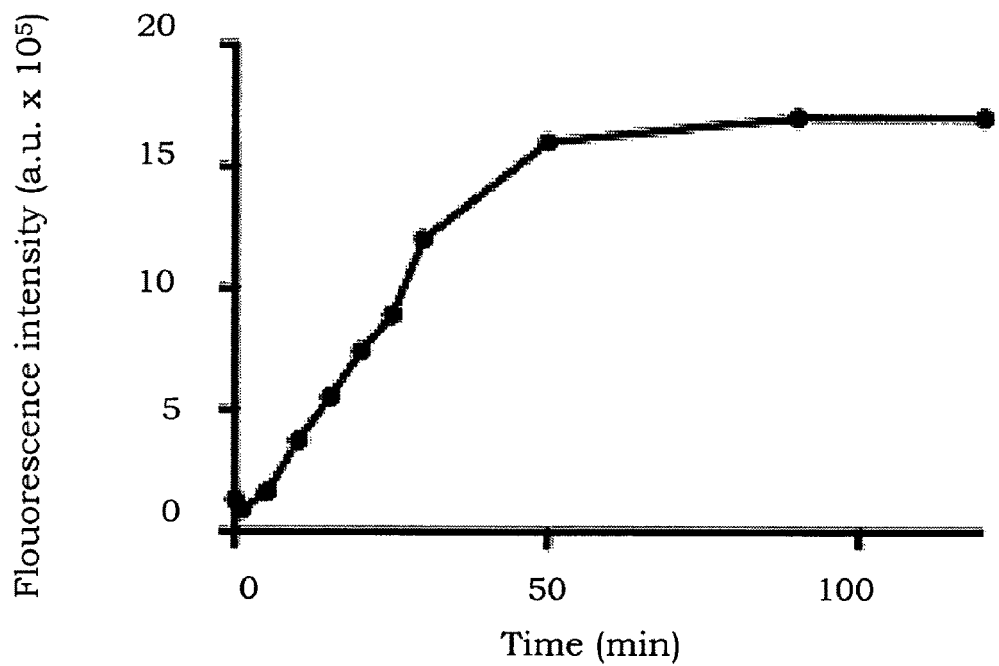
FIG. 7 illustrates time-dependence of the conversion of compound 4 to compound 7 at 37° C. MeOH/pH 7 buffer.
Figure 8:
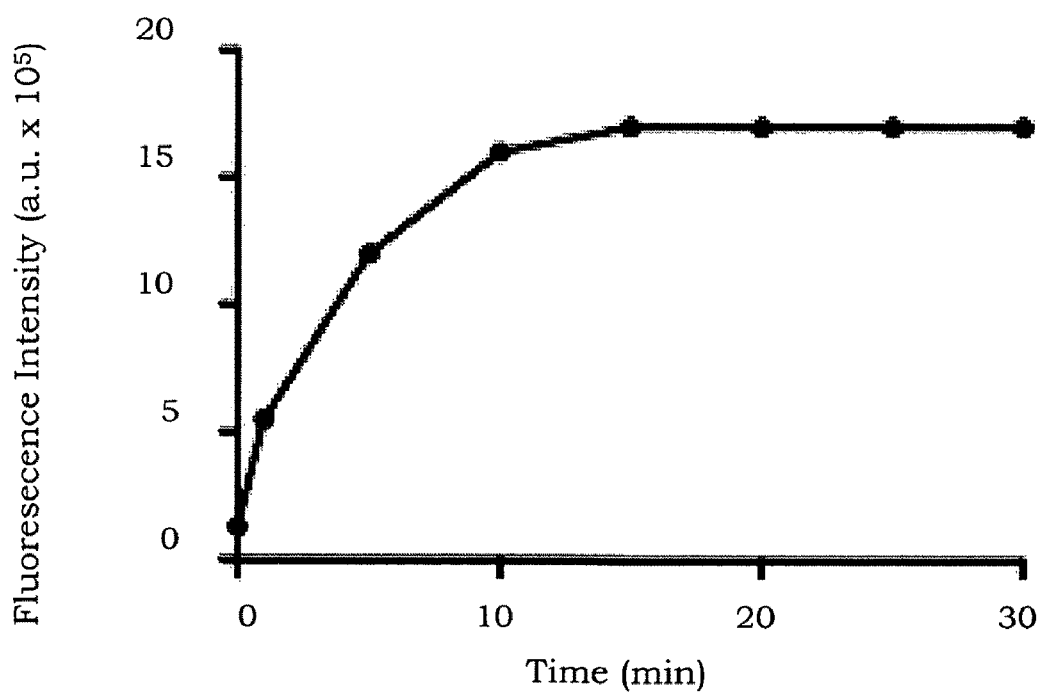
FIG. 8 illustrates Time-dependence of the conversion of compound 4 to compound 7 at 37° C. in 10% FBS in RPMI-1640 cell culture media/pH 7 buffer.

FIG. 7 illustrates time-dependence of the conversion of compound 4 to compound 7 in cell culture media at 37° C. MeOH/pH 7 buffer. See above for conditions. Solution A ([compound 4]$_{final}$=12.5 μM) was added to a mixture of 10% FBS in RPMI-1640 cell culture media/pH 7 buffer ([$PO_4^{3-}$]=5 mM) (1:3) (4.0 mL), and the sample was exposed to ozone (~5 μM) at 24° C. followed by incubation at 37° C. Aliquots of the reaction mixture were taken out at various times for fluorescence measurement (FIG. 8). The conversion of compound 4 to compound 7 requires 15-20 minutes for completion, but <5 minutes is sufficient to observe fluorescence signal. Although the exact mechanism of this enhancement is not known, catalysis of a β-elimination by action of bovine serum albumin has been previously reported.

FIG. 8 illustrates Time-dependence of the conversion of compound 4 to compound 7 at 37° C. in 10% FBS in RPMI-1640 cell culture media/pH 7 buffer. See above for conditions.

Figure 9:
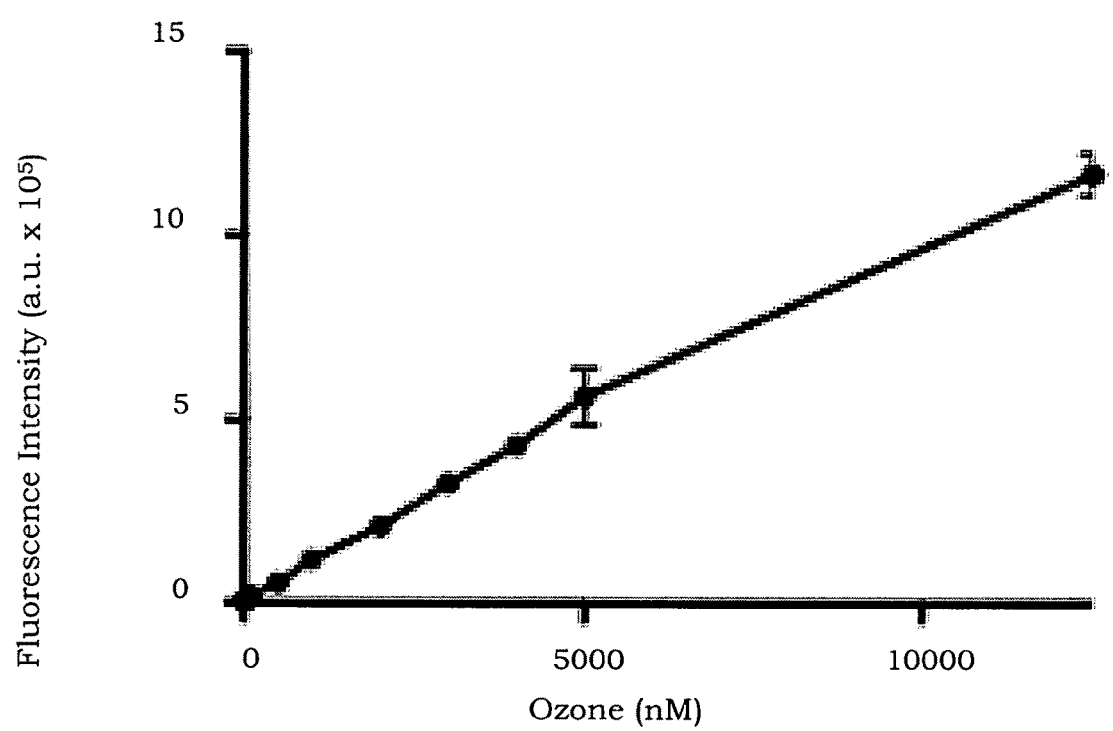
FIG. 9 illustrates the correlation between fluorescence intensity ($\lambda_{em}$=523 nm) and ozone in MeOH/pH 7 buffer (5:95)

Concentration dependence. Ozone solutions were prepared in pH 6 buffer and the concentrations were determined by UV absorption ($\lambda_{max}$=258 nm; ε=2900 l mol$^{-1}$ cm$^{-1}$. Solution A (5.0 μL, [compound 4]$_{final}$=12.5 μM) was added to a mixture of MeOH/pH 7 buffer ([$PO_4^{3-}$]=5 mM) (5:95) (4.0 mL), and the samples were exposed to varying amounts of ozone at 24° C. followed by 1 hour incubation at 37° C. The samples were diluted 10-fold with pH 7.0 buffer ([$PO_4^{3-}$]=5 mM) before fluorescence measurement to maintain linearity with respect to fluorescence signal (see FIG. 9 for the linearity between 0 and 12.5 μM). FIG. 9 illustrates the correlation between fluorescence intensity ($\lambda_{em}$=523 nm) and [ozone] in MeOH/pH 7 buffer (5:95). The background signal is 0.0377× 10$^5$. See above for conditions. For each experiment, triplicate replicas were performed. Error bars were determined from the calculated mean and standard deviation (Prism 5.0a, GraphPad Software, Inc.).

Ozone detection in the presence of antioxidants. Solution A (5.0 μL, [compound 4]$_{final}$=12.5 μM) and solutions E-G (E: 20.0 μL, [Ascorbic acid]$_{final}$=50 μM; F, G: 40.0 μL, [Glutathione/Uric acid]$_{final}$=100 μM) were added to a mixture of MeOH/pH 7 buffer ([$PO_4^{3-}$]=5 mM) (5:95) (4.0 mL), and the samples were exposed to ozone (~5 μM) at 24° C. followed by 1 hour incubation at 37° C. before fluorescence measurement. For each experiment, triplicate replicas were performed. FIG. 2C error bars were determined from the calculated mean and standard deviation (Prism 5.0a, GraphPad Software, Inc.).

Ozone detection in human pleural fluid. Human pleural fluid (1.0 mL) was diluted in pH 7 buffer ([$PO_4^{3-}$]=5 mM) (3.0 mL). Solution A (5.0 μL, [compound 4]$_{final}$=12.5 μM) was added to the resulting human pleural fluid mixture, and the samples were exposed to ozone (~5 μM) at 24° C. followed by 1 hour incubation at 37° C. before fluorescence measurement. The experiment was performed in triplicate with an illustration of one of the tests represented in FIG. 2D.

Ozone detection in human serum. Human serum (1.0 mL) was diluted in pH 7 buffer ([$PO_4^{3-}$]=5 mM) (3.0 mL). Solution A (5.0 μL, [compound 4]$_{final}$=12.5 μM) was added to the resulting human serum mixture, and the samples were exposed to ozone (~5 μM) at 24° C. followed by 1 hour incubation at 37° C. before fluorescence measurement. The experiment was performed in triplicate with an illustration of one of the tests represented in FIG. 2E.

Figure 10:
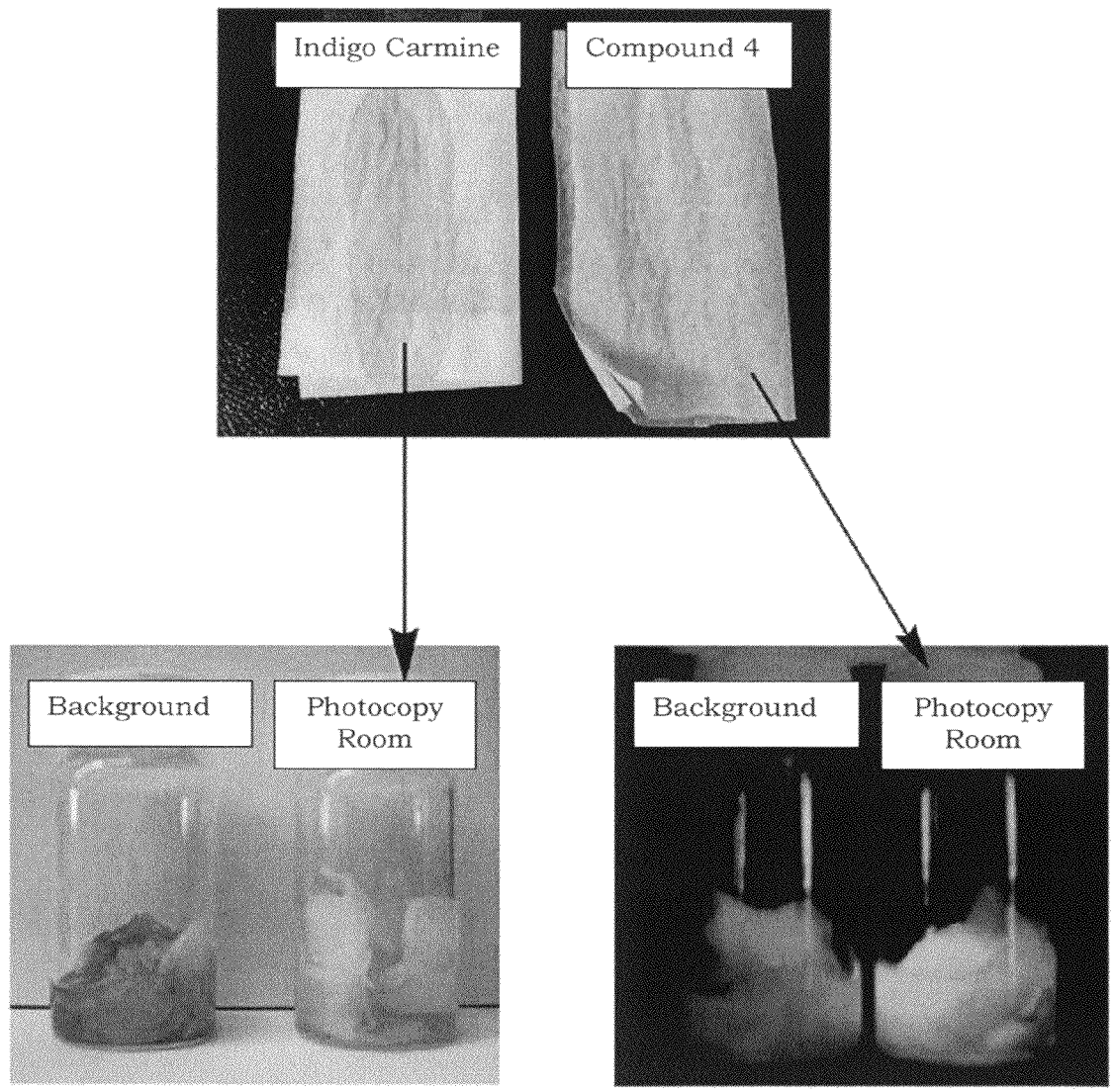
FIG. 10 are photographic illustrations of results of Ozone detection tests in indoor air using the present invention.
Figure 11A:
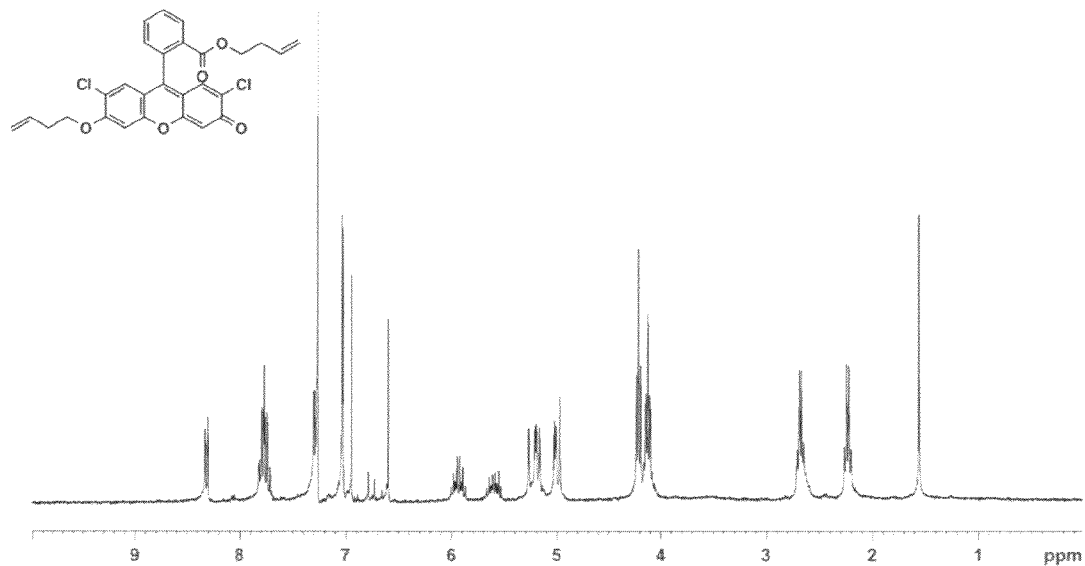
FIG. 11A is the $^1$H NMR spectrum of compound 3: $CDCl_3$, 293K, 300 MHz.
Figure 11B:
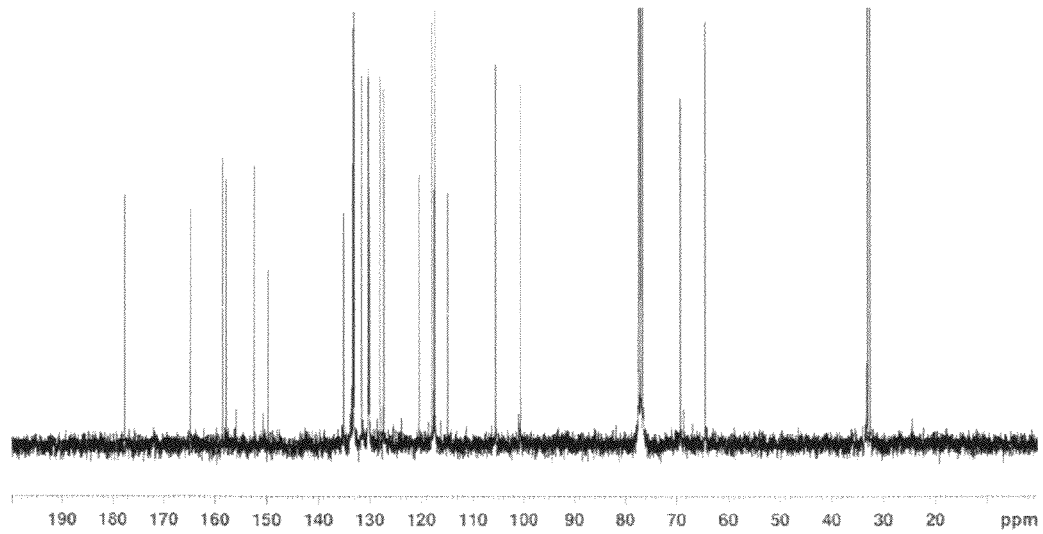
FIG. 11B is the $^{13}$C NMR spectrum of compound 3: $CDCl_3$, 293K, 75 MHz.
Figure 12A:
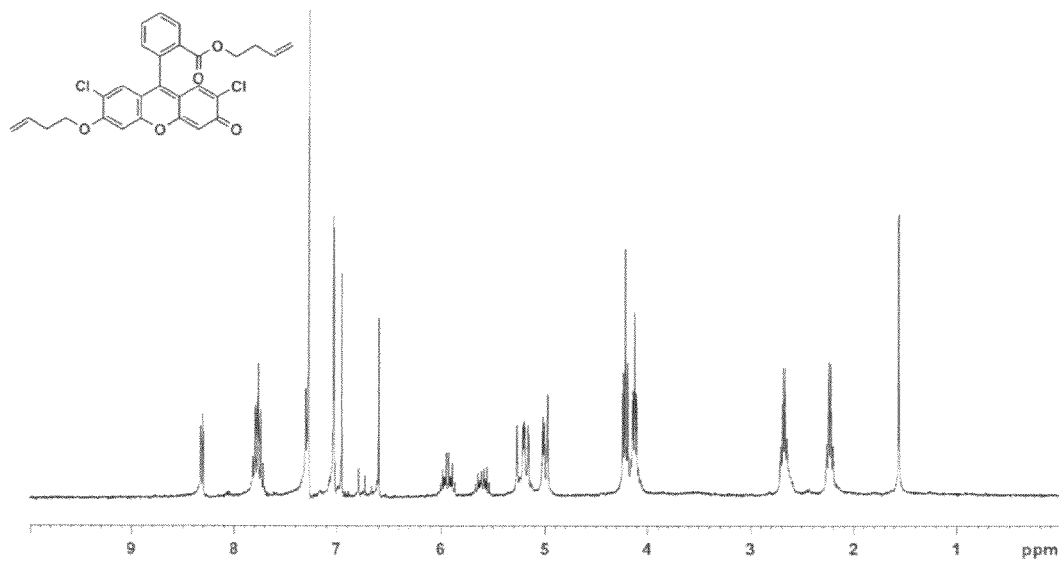
FIG. 12A is the $^1$H NMR spectrum of compound 4: $CDCl_3$, 293K, 300 MHz.
Figure 12B:
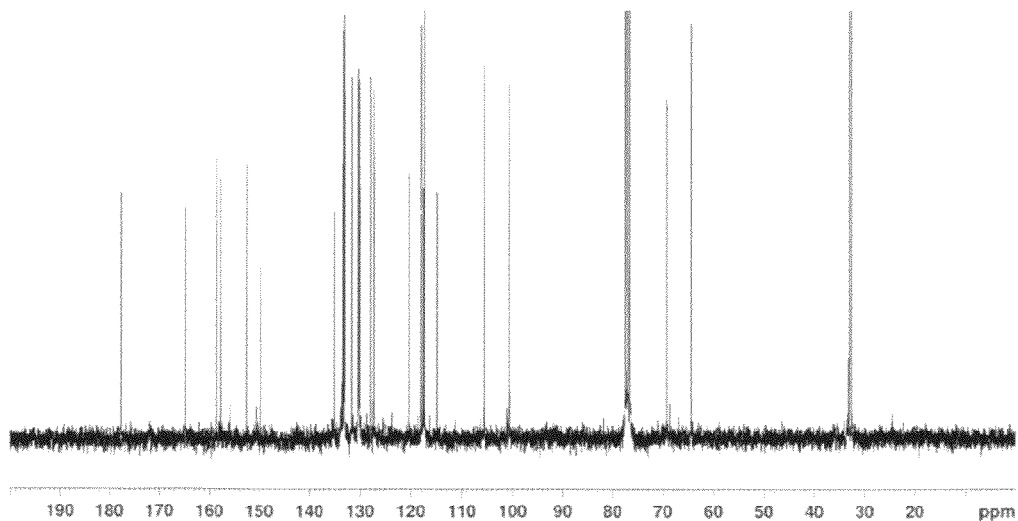
FIG. 12B is the $^{13}$C NMR spectrum of compound 4: $CDCl_3$, 293K, 75 MHz.
Figure 13A:
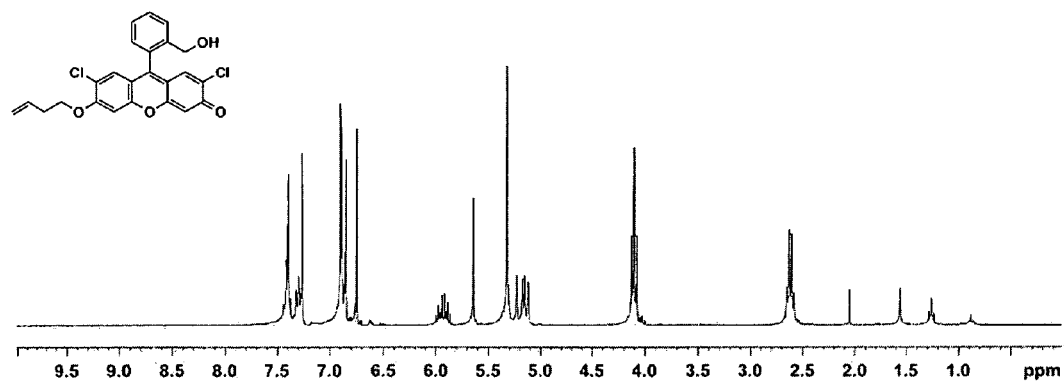
FIG. 13A is the $^1$H NMR spectrum of compound 8: $CDCl_3$, 293K, 300 MHz.
Figure 13B:
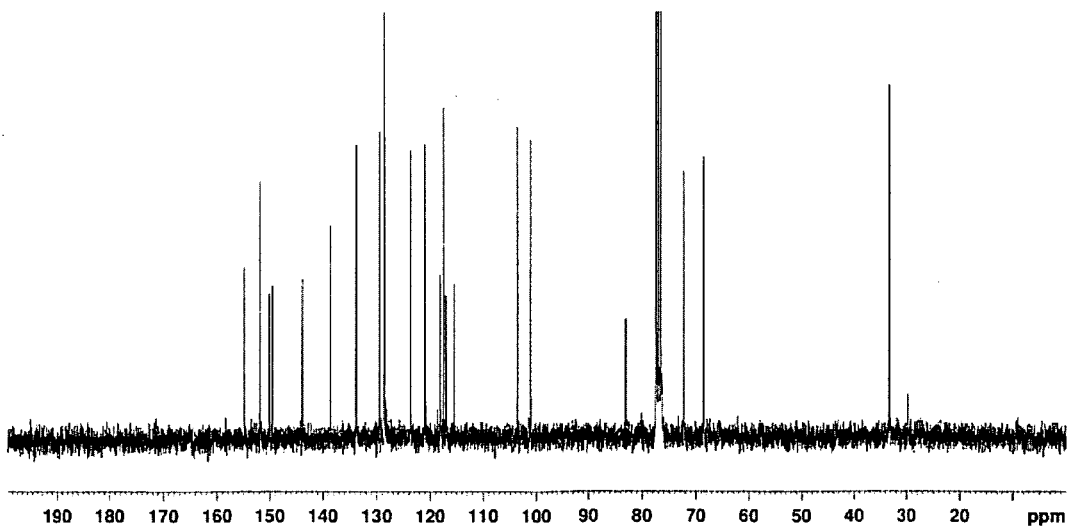
FIG. 13B is the $^{13}$C NMR spectrum of compound 8: $CDCl_3$, 293K, 75 MHz.

Ozone detection in indoor air. FIG. 10 are photographic illustrations of results of Ozone detection tests in indoor air using the present invention. The top photograph is a Kimwipe® before placing into photocopy room for 8 hours. The bottom photographs are a Kimwipe® in buffer for absorbance and fluorescence measurement, wherein the left photograph is an indigo carmine taken in room light), and the right photograph is compound 4 taken under long-range UV lamp. One adsorbent paper (Kimwipe®) was cut into two 11×9 cm pieces. Solution A (50 µL, 500 nmol of compound 4) was added to one portion of the Kimwipe® and allowed to dry (FIG. 10, top right). Solution B (50 µL, 500 nmol of indigo carmine) was added to the other portion of the Kimwipe® and allowed to dry (FIG. 10, top left). After overnight drying in a laboratory drawer, the paper strips were moved to a poorly ventilated photocopy room (2 photocopiers and 2 laser printers) for 8 hours. The controls remained in the laboratory drawer. After 8 hours, the samples were placed into a scintillation vial, and the dyes were eluted with pH 7 buffer (6.0 mL) (~5 min) before fluorescence and absorbance measurement. For each compound, triplicate replicas were performed. FIGS. 3C-D error bars were determined from the calculated mean and standard deviation (Prism 5.0a, GraphPad Software, Inc.).

Ozone detection in ambient air. Solution A (5.0 µL, [compound 4]$_{final}$=12.5 µM) was added to a mixture of MeOH/pH 7 buffer ([PO$_4^{3-}$]=5 mM) (5:95) (4.0 mL), and 4 samples were placed in 4 outdoor areas throughout University of Pittsburgh campus for 8 hours (high temperature=32.2° C.; AQI=43; PM2.5=64) on Jun. 6, 2008. The samples were not exposed to direct sunlight. The locations are described below. For each location, triplicate replicas were performed. FIGS. 3A-B error bars were determined from the calculated mean and standard deviation (Prism 5.0a, GraphPad Software, Inc.).

| Sample | Location (See the map: http://maps.google.com/?ie=UTF8&ll=40.444612,-79.955739&spn=0.00783,0.009527&t=h&z=17&layer=t) |
|---|---|
| Background | A negative control was prepared in the same manner but incubated at 37° C. in a closed vial for 8 h. |
| A | Corner of Forbes Avenue* (3 lane road) and South Bouquet Street (2 lane road) next to a lane of traffic frequently traveled by cars and buses |
| B | Corner of Fifth Avenue* (4 lane road) and Bigelow Boulevard (4 lane road) next to a lane of traffic frequently traveled by cars and buses |
| C | In a tree ~200 m from Fifth Avenue (University Drive/Parkman Avenue) |
| D | Outside a 12$^{th}$ floor window of Chevron Science Center, which is ~200 m from Fifth Avenue (the corner between University Drive and Parkman Avenue) |

*Forbes and Fifth Avenues are two of the most heavily traveled streets in Pittsburgh, Pennsylvania Air Pollutant Specificity:

Acids: HNO$_3$ or H$_2$SO$_4$ (10 µL of 0.1 M solution; [acid]$_{final}$=250 µM) and solution A (5.0 µL, [compound 4]$_{final}$=12.5 µM) were added to a mixture of MeOH/pure water solution (5:95) (4.0 mL), and the samples were incubated at 37° C. for 30 minutes before fluorescence measurement. For each experiment, triplicate replicas were performed with an illustration of one of the tests represented in FIG. 3B.

Metals: Pb, Pd or Pt solution (40 µL of 10 µM solution; [Metal]$_{final}$=100 nM) and solution A (5.0 µL, [compound 4]$_{final}$=12.5 µM) were added to a mixture of MeOH/pH 7 buffer ([PO$_4^{3-}$]=5 mM) (5:95) (4.0 mL), and the samples were incubated at 37° C. for 30 minutes before fluorescence measurement. For each experiment, triplicate replicas were performed with an illustration of one of the tests represented in FIG. 3B.

In another embodiment of the invention, human bronchial epitelial cells were incubated with compound 4 to determine ozone's role in cell biology. Although compound 4 was cell permeable, it was found that is had been converted to a fluorescent compound inside the cells in the absences of external ozone within ten minutes. Based on studies why compound 4 and structurally related compounds are not fluorescent, it is believed that the hydroxymethyl group 4 may have been oxidized to give a more electron-withdrawing group, possible a carboxyl or aldehyde group, and so emit a strong fluorescence signal. To circumvent such an oxidation event, compound 8 was prepared specific for ozone. Compound 8 is nearly non-fluorescent and thus used for the live-cell experiment. Unlike compound 4, compound 8 remained weakly fluorescent within the cells. Once a steady baseline signal had been established and maintained for five minutes, ozone gas was generated within the airtight environmental chamber that housed the cell-culture dishes, and fluorescent signals were monitored using live-cell microscopy for approximately 15 minutes. FIGS. 16A-H show a time-dependent increase in fluorescent emissions occurred inside the cells after ozone generation, which indicates that ozone can penetrated through cell membranes.

FIGS. 16A-H are photographs of live-cell imaging of human bronchial epithelial cells in the presence of ozone using compound 8. The left-hand panels (FIGS. A-E) are pseudocolour images that indicate the changes in emission intensity over time, and the right-hand panels show differential interference contrast images of the bronchial epithelial cells. FIG. 16A is before the addition of compound 8 (0 seconds). FIG. 16B illustrates the cell at 107 seconds that is a steady state intensity reached with compound 8 at 250 nM. FIG. 16C illustrates the cell at 326 seconds when ozone flow is started. FIG. 16D illustrates the cell at 536 seconds with the emission intensity increasing. FIG. 16E illustrates the cell at 675 seconds when emission maximum is reached. FIG. 16F illustrates the cell at 820 seconds when the cell starts to die. FIG. 16G illustrates the cell at 969 seconds where the cell emission continues to fall. FIG. 16H illustrates the cell at 1148 seconds when the ozone flow is stopped.

Figure 14:
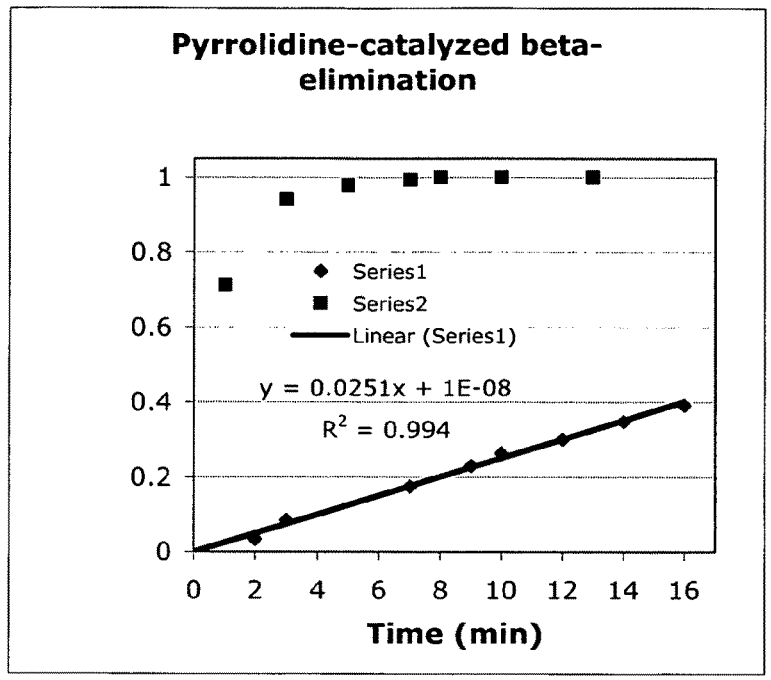
FIG. 14 illustrates test data of another embodiment of the invention (Series 1: pyrrolidine-catalyzed conversion of aldehyde 6 to compound 7) and comparative data (Series 2: no pyrrolidine)

Another embodiment of the present invention reduces the processing period to within four (4) minutes using pyrrolidine as a catalyst and concentrated pH 9 borate buffer as media. FIG. 14 illustrates the data of the invention (Series 2: pyrrolidine-catalyzed conversion of aldehyde 6 to compound 7) and comparative data (Series 1: no pyrrolidine). The conditions are [pyrrolidine]=45 mM, [aldehyde 6]=10 nM, MeOH/500 mM borate pH 9 buffer (5:95), 24° C. The Series 1 data linear correlation is (y=0.0251x+1E-08, R$^2$=0.994). The method can be employed using pyrrolidine at 0-1M, aldehyde 6 at 1 nM-1M, in a mixture of water-soluble organic solvents (e.g., MeOH, EtOH, iPrOH, MeCN, 1,4-dioxane, THF, DMSO, DMF) and pH 4-10 buffer in 0.1-80:99.9-20 ratios.

Figure 15:
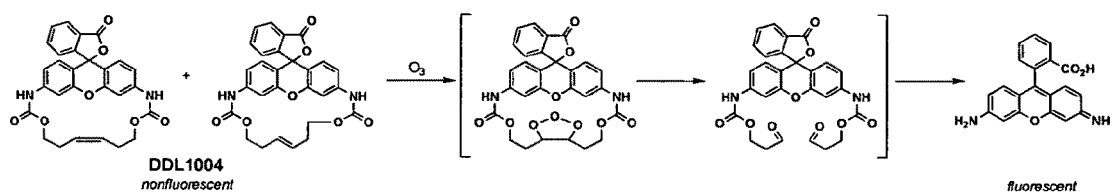
FIG. 15 is a DDL1004 formulation mixture of the $H_{cis}$ and $H_{trans}$ compounds.

FIG. 15 is DDL1004 mixture can replace compound 4 to detect Ozone. This is a mixture of the H$_{cis}$ and H$_{trans}$ compounds.

While the disclosure has been described in detail and with reference to specific embodiments thereof, it will be apparent to one skilled in the art that various changes and modifications can be made therein without departing from the spirit and scope of the embodiments. Thus, it is intended that the present disclosure cover the modifications and variations of this disclosure provided they come within the scope of the appended claims and their equivalents.

What is claimed is:

1. A method of detecting ozone in a sample comprising the steps of:
   1) contacting the sample with a fluorophore capable of undergoing allylic ether or allylic ester cleavage, wherein the fluorophore is a compound having a formula

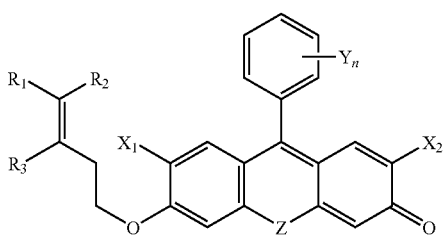

(I)

where $X^1$ and $X^2$ are each independently hydrogen, homoallyl group, or halogen;
Z is O, S, Se, or NR', wherein R' is a hydrogen or an homoallyl group;
n is an integer from 1 to 5;
each Y is independently hydrogen, or a functional group; and
$R^1$, $R^2$, and $R^3$ are independently either hydrogen atom, homoallyl, or aryl groups that may contain one or more further substitutions; and
   2) detecting fluorescence in the sample.

2. The method of claim 1, wherein the compound has a formula

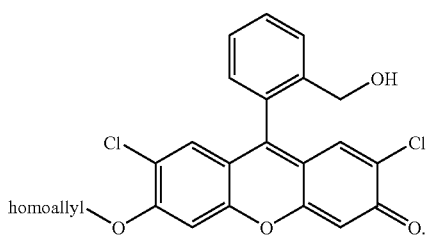

(II)

3. The method of claim 1, wherein Y is $CH_2OH$.

4. The method of claim 3, wherein at least one of $X^1$ and $X^2$ is Cl.

5. The method of claim 4, wherein at least one of R1, $R^2$, and $R^3$ is hydrogen.

6. The method of claim 1, wherein the sample is a biological sample selected from the group consisting of cells, whole blood, plasma, serum, saliva, urine, sweat, tears, cerebrospinal fluid and solid tissue.

7. The method of claim 1, wherein the sample is water or air.

8. The method according to claim 1, further comprising the step of adding pyrrolidine as a catalyst.

9. The method according to claim 8, wherein the step of adding pyrrolidine further comprises adding up to 1M of the pyrrolidine at 0-1M and about 1 nM to about 1M of aldehyde in a mixture of water-soluble organic solvents and buffer having pH 4-11.

10. The method according to claim 9, wherein the ratio of pyrrolidine, aldehyde, and water-soluble organic solvents to buffer is about 0.1-80:99.9-20.

11. The method according to claim 9, wherein the water-soluble organic solvents are selected from the group consisting of MeOH, EtOH, iPrOH, MeCN, 1,4-dioxane, THF, DMSO, and DMF.

12. A method of detecting ozone in a sample comprising the steps of:
   1) contacting the sample with a fluorophore capable of undergoing allylic ether or allylic ester cleavage, wherein the fluorophore is a compound having a formula (III)

where X is hydrogen, alkyl group, or halogen;
n is an integer from 1 to 2;
each Y is independently hydrogen, or a functional group; and
$R^1$, $R^2$, and $R^3$ are independently either hydrogen atom, alkyl, or aryl groups that may contain one or more further substitutions; and
   2) detecting fluorescence in the sample.

13. The compound of claim 12, wherein Y is $CH_2OH$.

14. The compound of claim 13, wherein at least one of $X^1$ or $X^2$ is Cl.

15. The compound of claim 14, wherein at least one of $R^1$, $R^2$, and $R^3$ is hydrogen.

16. The method according to claim 12, further comprising the step of adding pyrrolidine as a catalyst.

17. The method according to claim 16, wherein the step of adding pyrrolidine further comprises adding up to 1M of the pyrrolidine at 0-1M and about 1 nM to about 1M of aldehyde in a mixture of water-soluble organic solvents and buffer having pH 4-11.

18. The method according to claim 17, wherein the ratio of pyrrolidine, aldehyde, and water-soluble organic solvents to buffer is about 0.1-80:99.9-20.

19. The method according to claim 17, wherein the water-soluble organic solvents are selected from the group consisting of MeOH, EtOH, iPrOH, MeCN, 1,4-dioxane, THF, DMSO, and DMF.

20. The method of claim 12, wherein the sample is a biological sample selected from the group consisting of cells, whole blood, plasma, serum, saliva, urine, sweat, tears, cerebrospinal fluid and solid tissue.

21. The method of claim 12, wherein the sample is water or air.

22. A method of detecting ozone in a sample comprising the steps of:
1) contacting the sample with a fluorophore capable of undergoing allylic ether or allylic ester cleavage, wherein the fluorophore is a compound having a formula:

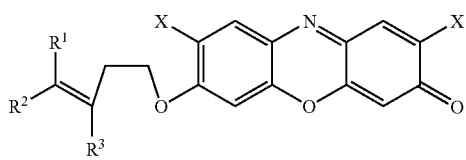

where each X is independently hydrogen, alkyl group, or halogen;
n is an integer from 1 to 2;
each Y is independently hydrogen, or a functional group; and
$R^1$, $R^2$, and $R^3$ are independently either hydrogen atom, alkyl, or aryl groups that may contain one or more further substitutions; and
2) detecting fluorescence in the sample.

23. The compound of claim 22, wherein Y is $CH_2OH$.

24. The compound of claim 23, wherein at least one of $X^1$ or $X^2$ is Cl.

25. The compound of claim 24, wherein at least one of $R^1$, $R^2$, and $R^3$ is hydrogen.

26. The method according to claim 22, further comprising the step of adding pyrrolidine as a catalyst.

27. The method according to claim 26, wherein the step of adding pyrrolidine further comprises adding up to 1M of the pyrrolidine at 0-1M and about 1 nM to about 1M of aldehyde in a mixture of water-soluble organic solvents and buffer having pH 4-11.

28. The method according to claim 27, wherein the ratio of pyrrolidine, aldehyde, and water-soluble organic solvents to buffer is about 0.1-80:99.9-20.

29. The method according to claim 27, wherein the water-soluble organic solvents are selected from the group consisting of MeOH, EtOH, iPrOH, MeCN, 1,4-dioxane, THF, DMSO, and DMF.

30. The method of claim 22, wherein the sample is a biological sample selected from the group consisting of cells, whole blood, plasma, serum, saliva, urine, sweat, tears, cerebrospinal fluid and solid tissue.

31. The method of claim 22, wherein the sample is water or air.

32. A method of detecting ozone in a sample comprising the steps of:
a) providing a non-fluorescent fluorophore in a mixture water-soluble organic solvents and buffer to form the sample, wherein the non-fluorescent fluorophore has a formula

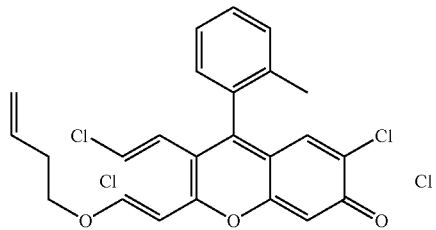 [SMILES: C=CCCO/C=C/c1oc2cc(=O)c(Cl)cc-2c(-c2ccccc2C)c1/C=C/Cl ; Cl ; Cl]

b) exposing the sample to ozone;
c) incubating the sample at a predetermined temperature for a predetermined time; and
d) measuring the fluorescence of the sample for the detection of ozone in human cells.

33. The method according to claim 32, further comprising the step of adding pyrrolidine as a catalyst.

34. A method of detecting ozone in a sample comprising the steps of:
a) providing a non-fluorescent fluorophore in a mixture water-soluble organic solvents and buffer to form the sample, wherein the non-fluorescent fluorophore has a formula

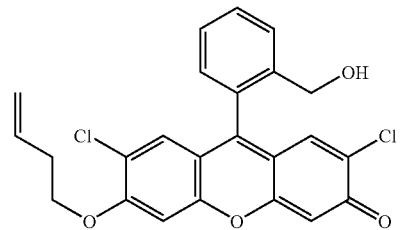 [SMILES: C=CCCOc1cc2oc3cc(=O)c(Cl)cc-3c(-c3ccccc3CO)c2cc1Cl]

b) exposing the sample to ozone;
c) incubating the sample at a predetermined temperature for a predetermined time; and
d) measuring the fluorescence of the sample for the detection of ozone in air samples.

35. The method according to claim 34, further comprising the step of adding pyrrolidine as a catalyst.

36. A method of detecting ozone in an indoor air sample comprising the steps of:
a) providing an adsorbent paper having a non-fluorescent fluorophore being disposed on a portion of the adsorbent paper, wherein the non-fluorescent fluorophore has a formula

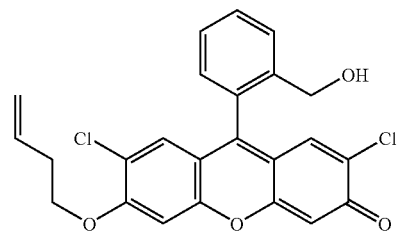 [SMILES: C=CCCOc1cc2oc3cc(=O)c(Cl)cc-3c(-c3ccccc3CO)c2cc1Cl]

b) exposing the sample to ozone for a predetermined time;
c) placing the samples into a scintillation vial and eluting the dyes before fluorescence and absorbance measurement; and d) measuring the fluorescence and absorbance of the sample.

37. The method according to claim 36, further comprising the step of adding pyrrolidine as a catalyst to the adsorbent paper.

38. A method of detecting ozone in a sample comprising the steps of:
   a) providing a non-fluorescent fluorophore in a mixture water-soluble organic solvents and buffer to form the sample, wherein the non-fluorescent fluorophore has a formula

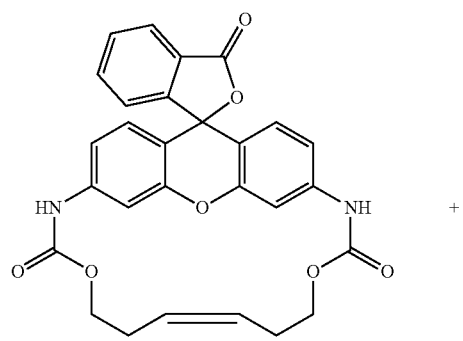

+

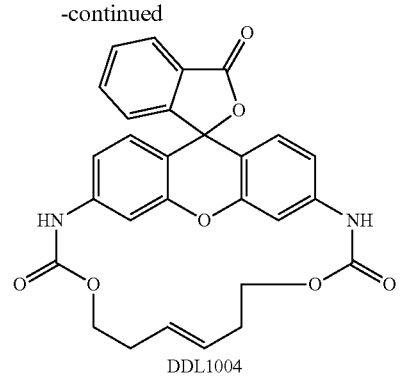

DDL1004 b) exposing the sample to ozone;
   c) incubating the sample at a predetermined temperature for a predetermined time; and
   d) measuring the fluorescence of the sample for the detection of ozone in air samples.

39. The method according to claim 38, further comprising the step of adding pyrrolidine as a catalyst.

* * * * *